US005356623A

United States Patent [19]
von Tersch et al.

[11] Patent Number: 5,356,623
[45] Date of Patent: Oct. 18, 1994

[54] BACILLUS THURINGIENSIS CRYET1 TOXIN GENE AND PROTEIN TOXIC TO LEPIDOPTERAN INSECTS

[75] Inventors: Michael A. von Tersch; José M. González, both of Ewing Township, N.J.

[73] Assignee: Ecogen Inc., Langhorne, Pa.

[21] Appl. No.: 32,364

[22] Filed: Mar. 17, 1993

[51] Int. Cl.$^5$ .................. C12N 1/21; C12N 1/22; C12N 15/32; A01N 63/00
[52] U.S. Cl. .................. 424/93.2; 536/23.71; 435/320.1; 435/252.3; 435/252.31; 435/69.1; 424/93.461
[58] Field of Search .................. 536/23.71; 435/320.1, 435/252.1, 252.3, 252.31, 172.3, 69.1; 800/205; 424/93 L, 93 A

[56] References Cited

U.S. PATENT DOCUMENTS 5,064,648 11/1991 Hickle et al. .................. 424/93 R

FOREIGN PATENT DOCUMENTS 289479 11/1988 European Pat. Off. .
295156 12/1988 European Pat. Off. .
358557  3/1990 European Pat. Off. .
367474  5/1990 European Pat. Off. .
401979 12/1990 European Pat. Off. .
405810  1/1991 European Pat. Off. .
462721 12/1991 European Pat. Off. .
90-13651 11/1990 PCT Int'l Appl. .
91-16434 10/1991 PCT Int'l Appl. .

OTHER PUBLICATIONS

Gleave et al., *J. Gen. Microbiol.* 138: 55–62 (1992) "Identification of an insecticidal crystal protein from *Bacillus thuringiensis* DSIR517 with significant sequence differences from previously described toxins".
Smulevitch et al., *FEBS Lett* 293:25–28(1991) "Nucleotide sequence of a novel δ-endotoxin gene *crylg* of *Bacillus thuringiensis* ssp. *galleriae*".
Chambers et al., *J. Bacteriol.* 173: 3966–3976 (1991) "Isolation and Characterization of a Novel Insecticidal Crystal Protein Gene from *Bacillus thuringiensis* subsp. *aizawai*".
Perlak et al., *Proc. Natl. Acad. Sci. USA* 88: 3324–3328 (1991) "Modification of the coding sequence enhances plant expression of insect control protein genes".
Von Tersch et al., *Appl. Environ. Microbiology* 57: 349–358 (1991) "Insecticidal Toxins from *Bacillus thuringiensis* subsp. *kenvae:* Gene Cloning and Characterization and Comparison with *B. thuringiensis* subsp. *kurstaki* CryIA(c) Toxins".
Visser et al., *J. Bacteriol.* 172: 6783–6788 (1990) "A Novel *Bacillus thuringiensis* Gene Encoding a *Spodoptera exigua*-Specific Crystal Protein".
Hodgman et al., *J. DNA Sequencing and Mapping* 1: 97–106 (1990) "Models for the structure and function of the *Bacillus thuringiensis* δ-endotoxins determined by compilational analysis".
Höfte et al., *Microbiol. Rev.* 53: 242–255 (1989) "Insecticidal Crystal Proteins of *Bacillus thuringiensis*".
Ge et al., *Proc. Natl. Acad. Sci. USA* 86: 4037–4041 (1989) "Location of the *Bombyx mori* specificity domain on a *Bacillus thuringiensis* δ-endotoxin protein".
Sanchis et al., *Molecular Microbiol.* 3: 229–238 (1989) "Nucleotide sequence and analysis of the N-terminal coding region of the *Spodoptera*-active δ-endotoxin gene of *Bacillus thuringiensis aizawai* 7.29".

(List continued on next page.)

*Primary Examiner*—Che S. Chereskin
*Attorney, Agent, or Firm*—Christopher Egolf; Alan S. Nadel

[57] ABSTRACT

A *Bacillus thuringiensis* strain isolate, designated EG5092, exhibits insecticidal activity against lepidopteran insects. A purified and isolated novel cryET1 toxin gene product from B.t. strain EG5092 exhibits specific insecticidal activity against *Plutella xylostella* (Diamondback moth). The cryET1 gene (SEQ ID NO:1) has a nucleotide base sequence illustrated in FIG. 1 and produces a CryET1 gene product (SEQ ID NO:2) having a deduced amino acid sequence illustrated in FIG. 1.

12 Claims, 13 Drawing Sheets

Masson, et al., *Nucl. Acids Res.* 17: 446 (1989) "Nucleotide sequence of a gene cloned from *Bacillus thuringiensis* subspecies *entomocidus* coding for an insecticidal protein toxic for *Bombyx mori*".

Haider et al., *Nucl. Acids Res.* 16: 10927 (1988) "Nucleotide sequence of a *Bacillus thuringiensis aizawai* IC1 entomocidal crystal protein gene".

Honée et al., *Nucl. Acids Res.* 16: 6240 (1988) "Nucleotide sequence of crystal protein gene isolated from *B. thuringiensis* subspecies *entomocidus* 60.5 coding for a toxin highly active against *Spodoptera* species".

Brizzard et al., *Nucl. Acids Res.* 16:2723–2724 (1988) "Nucleotide sequence of an additional crystal protein gene cloned from *Bacillus thuringiensis*".

Shimizu et al., *Agric. Biol. Chem.* 52: 1565–1573 (1988) "Cloning and Expression in *Escherichia coli* of the 135-kDa Insecticidal Protein Gene from *Bacillus thuringiensis* subsp. *aizawai* IPL7".

Visser et al., *Mol. Gen. Genet.* 212: 219–224 (1988) "Genes from *Bacillus thuringiensis entomocidus* 60.5 coding for insect-specific crystal proteins".

Donovan et al., *J. Biol. Chem.* 263: 561–567 (1988) "Amino Acid Sequence and Entomocidal Activity of the P2 Crystal Protein".

Fischoff et al., *Bio/Technology* 5: 807–813 (1987) "Insect Tolerant Transgenic Tomato Plants".

Ward et al., *Nucl. Acids Res.* 15: 7195 (1987) "Nucleotide sequence of a *Bacillus thuringiensis* var. *israelensis* gene encoding a 130 kDa delta-endotoxin".

Herrnstadt et al., *Gene* 57: 37–46 (1987) "Nucleotide sequence and deduced amino acid sequence of a coleopteran-active delta-endotoxin gene from *Bacillus thuringiensis* subsp. *san diego*".

Oeda et al., *Gene* 53: 113–119 (1987) "Nucleotide sequence of the insecticidal protein gene of *Bacillus thuringiensis* strain *aizawai* IPL7 and its high-level expression in *Escherichia coli*".

Hefford et al., *J. Biotechnology* 6: 307–322 (1987) "Sequence of a lepidopteran toxin gene of *Bacillus thuringiensis* subsp. *kurstaki* NRD-12".

Kondo et al., *Agric. Biol. Chem.* 51: 455–463 (1987) "Cloning and Nucleotide Sequencing of Two Insecticidal δ-Endotoxin Genes from *Bacillus thuringiensis* var. *kurstaki* HD-1 DNA".

Geiser et al., *Gene* 48: 109–118 (1986) "The hypervariable region in the genes coding for entomopathogenic crystal proteins of *Bacillus thuringiensis:* nucleotide sequence of the *kurhdl* gene of subsp. *kurstaki* HD1".

Wabiko et al., *DNA* 5:305–314 (1986) "*Bacillus thuringiensis* Entomocidal Protoxin Gene Sequence and Gene Product Analysis".

Höfte et al., *Eur. J. Biochem.* 161:273–280 (1986) "Structural and functional analysis of a cloned delta endotoxin of *Bacillus thuringiensis berliner* 1715".

Schnepf et al., *J. Biol. Chem.* 260: 6264–6272 (1985) "The Amino Acid Sequence of a Crystal Protein from *Bacillus thuringiensis* Deduced from the DNA Base Sequence*".

Adang et al., *Gene* 36:289–300 (1985) "Characterized full-length and truncated plasmid clones of the crystal protein of *Bacillus thuringiensis* subsp. *kurstaki* HD-73 and their toxicity to *Manduca sexta*".

Shibano et al., *Gene* 34:243–251 (1985) "Nucleotide sequence coding for the insecticidal fragment of the *Bacillus thuringiensis* crystal protein".

Carlton et al., "Plasmids and Delta-Endotoxin Production in Different Subspecies of *Bacillus thuringiensis*", pp. 246–252, in *Molecular Biology of Microbial Differentiation*, J. A. Hoch and P. Setlow, ed., American Society for Microbiology, Washington, D.C. (1985).

King et al., "*Heliothis Virescens*", in *Handbook of Insect Rearing*, Vol. II, P. Singh and R. F. Moore (eds.), pp. 323–328, Elsevier Science, Amsterdam, (1985).

Fitz-James et al., *J. Invertebr. Pathol.* 43: 47–58 (1984) "A Surface Net on Parasporal Inclusions of *Bacillus thuringiensis*".

Kaiser et al., *Science* 223: 249–255 (1984) "Amphiphilic Secondary Structure: Design of Peptide Hormones".

FIG. 1₁

```
CGT GTA TGT CCA GGT CGT GGA TAC ATC CTT CGT GTC ACA GCG TAC AAA    3248
Arg Val Cys Pro Gly Arg Gly Tyr Ile Leu Arg Val Thr Ala Tyr Lys
1010                        1015                    1020

GAG GGC TAC GGA GAA GGA TGC GTA ACG ATC CAT GAG ATC GAA GAC AAC    3296
Glu Gly Tyr Gly Glu Gly Cys Val Thr Ile His Glu Ile Glu Asp Asn
    1025                    1030                    1035         1040

ACA GAC GAA CTG AAG TTT AGA AAC TGT GAA GAG GGA GAT TAT TCA        3344
Thr Asp Glu Leu Lys Phe Arg Asn Cys Glu Glu Gly Asp Tyr Ser
        1045                    1050                    1055

AAC GAC ACA GGA ACG TGT AAT GAT TAT CCT GCA TCC CAA GGT GCA GCA    3392
Asn Asp Thr Gly Thr Cys Asn Asp Tyr Pro Ala Ser Gln Gly Ala Ala
    1060                    1065                    1070

GGC TGC GCA GAT GTA TGT AAT TCC CGT AAT GTT GGA TAT AAG GAT GCA    3440
Gly Cys Ala Asp Val Cys Asn Ser Arg Asn Val Gly Tyr Lys Asp Ala
        1075                    1080                    1085

TAT GAA ACG AAT ACC TCA GCA TCT GTT AAT TAC AAA CCG ACT TAC GAA    3488
Tyr Glu Thr Asn Thr Ser Ala Ser Val Asn Tyr Lys Pro Thr Tyr Glu
    1090                    1095                    1100

GAA GAA ACG TAT ACA GAT GTA CGA GAA GAT AAT CAT TGT GAA TAT GAC    3536
Glu Glu Thr Tyr Thr Asp Val Arg Glu Asp Asn His Cys Glu Tyr Asp
    1105                    1110                    1115         1120

AGA GGG TAT GTG AAT TAT CCA CCA TTA CCA GCT GGT TAT GTG ACA AAA    3584
Arg Gly Tyr Val Asn Tyr Pro Pro Leu Pro Ala Gly Tyr Val Thr Lys
    1125                    1130                    1135
```

FIG. 1A

```
AATGATACAA CCTAAATTTT CATATGTTAA ACAAGGTTAT ATGCTGAAAT ATAAAAAAAT    60
AAGTTGCATA TTGTGCATAA ATTCATAATA TAAATCATAC GTTTTAAAGT GTTGTGAAGA   120
AAGGAGTATC GAACTTTTAA AATTTTTTAT TTTAACCAAA GAGAAAGGGG TAACTT        176

ATG GAG ATA AAT AAT CAG AAC CAA TGC ATA CCA TAT AAT TGC TTA AGT     224
Met Glu Ile Asn Asn Gln Asn Gln Cys Ile Pro Tyr Asn Cys Leu Ser
 1                   5                  10                  15

AAT CCT GAG GAA GTA CTT TTG GAT GGG GAG AGG ATA TTA CCT GAT ATC     272
Asn Pro Glu Glu Val Leu Leu Asp Gly Glu Arg Ile Leu Pro Asp Ile
                20                  25                  30

GAT CCA GAA GTT TCT ATG TCG CTT TTG CAA TTT CTT TTG AAT AAC         320
Asp Pro Glu Val Ser Met Ser Leu Leu Gln Phe Leu Leu Asn Asn
            35                  40                  45

TTT GTT CCA GGG GGC TTT ATT TCA GGA TTA TTT GAT AAA ATA TGG         368
Phe Val Pro Gly Gly Phe Ile Ser Gly Leu Phe Asp Lys Ile Trp
    50                  55                  60

GGG GCT TTG AGA CCA TCT GAC TGG GAA TTA TTT CTT GCA CAA ATT GAA     416
Gly Ala Leu Arg Pro Ser Asp Trp Glu Leu Phe Leu Ala Gln Ile Glu
 65                  70                  75                  80

CAG TTG ATT GAT CAA GGT ATA GAA GCA ACA ACT AGA GCA AAA GCA ATC     464
Gln Leu Ile Asp Gln Gly Ile Glu Ala Thr Arg Val Arg Ala Lys Ile
                85                  90                  95

GCT GAA TTA GAA GGT TTA GGG AGA AGT TTT CAA CTA TAT GTA GAG GCA     512
Ala Glu Leu Glu Gly Leu Gly Arg Ser Phe Gln Leu Tyr Val Glu Ala
                100                 105                 110
```

FIG. 1B

| | | | | | | | | | |
|---|---|---|---|---|---|---|---|---|---|
| TTT | AAA | TGG | GAA | GAA | ACT | CCA | GAT | AAC | ACA | GCG | GCT | CGG | TCT | AGA | 560 |
| Phe | Lys | Trp | Glu | Glu | Thr | Pro | Asp | Asn | Thr | Ala | Ala | Arg | Ser | Arg | |
| | 115 | | | | | 120 | | | | 125 | | | | | |
| GTA | ACT | GAG | AGA | TTT | CGT | ATA | ATT | GAT | GCT | CAA | ATT | GAA | GCA | AAT | ATC | 608 |
| Val | Thr | Glu | Arg | Phe | Arg | Ile | Ile | Asp | Ala | Gln | Ile | Glu | Ala | Asn | Ile |
| 130 | | | | 135 | | | | 140 | | | | | | | |
| CCT | TCG | TTT | CGG | ATT | CCC | GGA | TTT | GAA | GTG | CCA | CTT | CTA | TCG | GTT | TAT | 656 |
| Pro | Ser | Phe | Arg | Ile | Pro | Gly | Phe | Glu | Val | Pro | Leu | Leu | Ser | Val | Tyr |
| 145 | | | | 150 | | | | 155 | | | | 160 | | | |
| GCT | CAA | GCA | GCT | AAT | TTG | CAT | CTC | GCT | CTA | TTA | AGA | GAT | TCT | GTT | ATT | 704 |
| Ala | Gln | Ala | Ala | Asn | Leu | His | Leu | Ala | Leu | Leu | Arg | Asp | Ser | Val | Ile |
| | | 165 | | | | | 170 | | | | | 175 | | | |
| TTC | GGA | AGA | TGG | GGA | TTG | ACG | ACT | ACA | AAT | GTC | AAT | GAT | ATC | TAT | 752 |
| Phe | Gly | Arg | Trp | Gly | Leu | Thr | Thr | Thr | Asn | Val | Asn | Asp | Ile | Tyr |
| | 180 | | | | | 185 | | | | 190 | | | | | |
| AAT | AGA | CAA | GTT | AAG | AGA | ATT | CAT | GAA | TAT | AGC | GAT | CAT | TGT | GTA | GAT | 800 |
| Asn | Arg | Gln | Val | Lys | Arg | Ile | His | Glu | Tyr | Ser | Asp | His | Cys | Val | Asp |
| 195 | | | | | 200 | | | | | 205 | | | | | |
| ACG | TAT | AAA | ACA | GAA | TTA | CGT | CTA | GGG | TTT | ACT | TCT | AGA | GCG | CAG | 848 |
| Thr | Tyr | Lys | Thr | Glu | Leu | Arg | Leu | Gly | Phe | Thr | Ser | Arg | Ala | Gln |
| 210 | | | | 215 | | | | | 220 | | | | | | |
| TGG | AAA | ATA | TAT | AAT | CAG | TTT | AGA | AGA | GAA | TTA | ACA | CTA | ACG | GTA | TTA | 896 |
| Trp | Lys | Ile | Tyr | Asn | Gln | Phe | Arg | Arg | Glu | Leu | Thr | Leu | Thr | Val | Leu |
| 225 | | | | | 230 | | | | | 235 | | | | | 240 |

FIG. 1c

```
GAT ATT GTC GCT GTT TTC CCG AAC TAT GAT GGT AAA CTG TAT CCG ATC    944
Asp Ile Val Ala Val Phe Pro Asn Tyr Asp Gly Lys Leu Tyr Pro Ile
                245                 250                 255

CAA ACA AAA TCT GAA TTA ACA AGA GAA ATT TAT ACA TCC CCA GTA TCC    992
Gln Thr Lys Ser Glu Leu Thr Arg Glu Ile Tyr Thr Ser Pro Val Ser
                260                 265                 270

GAA TAT TAT GGT GCT ATT AAT AAC TAT AAT CAA AAT GGT ATC CAA       1040
Glu Tyr Tyr Gly Ala Ile Asn Asn Tyr Asn Gln Asn Gly Ile Gln
        275                 280                 285

ACT GAA CGG CAG ATA AGG CAA CCA CAT CTT ATG GAC TTC TTT AAC ACC   1088
Thr Glu Arg Gln Ile Arg Gln Pro His Leu Met Asp Phe Phe Asn Thr
                290                 295                 300

ATG ACC ATG TAT ACA TCA TAT AAT AGA CGG GAA CGG TAT TAT TGG TCA GGA 1136
Met Thr Met Tyr Thr Ser Tyr Asn Arg Arg Glu Arg Tyr Tyr Trp Ser Gly
                305                 310                 315                 320

CTT GAA ATG ACG GCT TAT TTC ACA GGA TTT GCA GGA CCT CAA GTG TCA   1184
Leu Glu Met Thr Ala Tyr Phe Thr Gly Phe Ala Gly Pro Gln Val Ser
                325                 330                 335

TTC CCT TTA GCT GGG ACT AGA GGG GAT GCA GCT CCA CCA TTT AAT GTT   1232
Phe Pro Leu Ala Gly Thr Arg Gly Asp Ala Ala Pro Pro Phe Asn Val
                340                 345                 350

AGA AGT GTT AAT GAT GGA ATT TAT AGA ATA TTA TCG GCA CCA TTT TAT   1280
Arg Ser Val Asn Asp Gly Ile Tyr Arg Ile Leu Ser Ala Pro Phe Tyr
                355                 360                 365
```

FIG. 1D

```
TCA GCA CCT TTC TTA GGT ACC TCT GTA TTG GGC AGT CGT GGA GAA GAA    1328
Ser Ala Pro Phe Leu Gly Thr Ser Val Leu Gly Ser Arg Gly Glu Glu
370                 375                 380

TTT ATG TTT GCA CTT AAT ATT TCA CCC CCG CCA TCT GCA AGA TAC        1376
Phe Met Phe Ala Leu Asn Ile Ser Pro Pro Pro Ser Ala Arg Tyr
385                 390                 395                 400

AGA AAT CCT GGA ACA GTA GAT TCA CTA GTC AGC ATA CCG CCA CAG GAT    1424
Arg Asn Pro Gly Thr Val Asp Ser Leu Val Ser Ile Pro Pro Gln Asp
        405                 410                 415

AAT AGC GTG CCA CCA CAC AGG GGA TCT AGT CAT CGA TTA AGT CAT GTT    1472
Asn Ser Val Pro Pro His Arg Gly Ser Ser His Arg Leu Ser His Val
420                 425                 430

ACA ATG CGT AAT AGT TCA CCT ATA TTC CAC TGG ACA CAT CGC AGC GCA    1520
Thr Met Arg Asn Ser Pro Ile Phe His Trp Thr His Arg Ser Ala
        435                 440                 445

ACC ACT ACA AAT AGA ATT AAT TCA GAT GTT ATT ACG CAA ATT CCA ATG    1568
Thr Thr Thr Asn Arg Ile Asn Ser Asp Val Ile Thr Gln Ile Pro Met
450                 455                 460

GTA AAA GCA TAC AAT CTT CAT GCA GGT GCC ACT GTT GTT AGA GGA CCC    1616
Val Lys Ala Tyr Asn Leu His Ala Gly Ala Thr Val Val Arg Gly Pro
465                 470                 475                 480

GGG TTT ACA GGT GGT GAT ATC CTG AGA CGA ACA AGT AAT GGG ATG GTC    1664
Gly Phe Thr Gly Gly Asp Ile Leu Arg Arg Thr Ser Asn Gly Met Val
        485                 490                 495
```

FIG. 1E

```
GTA ACA CTA AGA GTA GAT GCC TCT GCA GTA AGG AAC CAA CGA TAT CGC   1712
Val Thr Leu Arg Val Asp Ala Ser Ala Val Arg Asn Gln Arg Tyr Arg
            500                 505                 510

ATA AGA TTC CGT TAT GCT GCA ACA AAT TTC TAT TTT GTC GTA AGG       1760
Ile Arg Phe Arg Tyr Ala Ala Thr Ser Asn Phe Tyr Phe Val Arg
    515                 520                 525

CGT GGG AAT CTT GGT GTT AAT GGT CGA GAG ATC ATG AAA ACA ATG AGT   1808
Arg Gly Asn Leu Gly Val Asn Gly Arg Glu Ile Met Lys Thr Met Ser
        530                 535                 540

ACA GGC GAG GAA TTA AAA TCT GCA TCT TTT GTT TTG GGA GAG TTT ATT   1856
Thr Gly Glu Glu Leu Lys Ser Ala Ser Phe Val Leu Gly Glu Phe Ile
    545                 550                 555                 560

ACG CCT TTT AAT TTT GAA AAT CAG GTT CCA CTT CAA ATA GAA ATA       1904
Thr Pro Phe Asn Phe Glu Asn Gln Val Pro Leu Gln Ile Glu Ile
        565                 570                 575

CAA TCA CTT TCT CCT GGG GGA GAG GTG TAT CTG GAC AAA ATT GAA TTC   1952
Gln Ser Leu Ser Pro Gly Gly Glu Val Tyr Leu Asp Lys Ile Glu Phe
            580                 585                 590

ATC CCA GCA GAT ACA ACA TTT GAA GCA GAA TAT GAT TTA GAA AGA GCG   2000
Ile Pro Ala Asp Thr Thr Phe Glu Ala Glu Tyr Asp Leu Glu Arg Ala
        595                 600                 605

CAG AAG GCG GTG AAT GCT CTG TTT ACT TCT ACG AAT CAA AGA GGA CTA   2048
Gln Lys Ala Val Asn Ala Leu Phe Thr Ser Thr Asn Gln Arg Gly Leu
    610                 615                 620
```

FIG. 1F

```
AAA ACA GAT GTA ACA GAT TAT CAC ATT GAT CAA GTA TCC AAT TTA GTC    2096
Lys Thr Asp Val Thr Asp Tyr His Ile Asp Gln Val Ser Asn Leu Val
625                 630                 635                 640

GAA TGT TTA TCG GAT GAA TTT TGT TTA GAT TGT GAA AAG AGA GAG TTG TCC    2144
Glu Cys Leu Ser Asp Glu Phe Cys Leu Asp Cys Glu Lys Arg Glu Leu Ser
                645                 650                 655

GAG AAA GTC AAA CAT GCG AAG CGA CTC AGT GAT GAA AGA AAC TTA CTG    2192
Glu Lys Val Lys His Ala Lys Arg Leu Ser Asp Glu Arg Asn Leu Leu
        660                 665                 670

CAA GAT CCA AAC TTC ACA TCC ATC AAT GGA CAA CTA GAC CGT GGA TGG    2240
Gln Asp Pro Asn Phe Thr Ser Ile Asn Gly Gln Leu Asp Arg Gly Trp
            675                 680                 685

AGA GGA AGT ACG GAT ATT ACC ATC CAA GGA AAT GAC GTA TTC AAA    2288
Arg Gly Ser Thr Asp Ile Thr Ile Gln Gly Gly Asn Asp Val Phe Lys
690                 695                 700

GAA AAT TAC GTC ACA CTA CCA GGT ACC TTT GAT GAG TGT TAT CCA ACG    2336
Glu Asn Tyr Val Thr Leu Pro Gly Thr Phe Asp Glu Cys Tyr Pro Thr
705                 710                 715                 720

TAT TTG TAT CAA AAA ATA GAT GAG TCA AAA TTA AAA GCC TAT ACT CGC    2384
Tyr Leu Tyr Gln Lys Ile Asp Glu Ser Lys Leu Lys Ala Tyr Thr Arg
        725                 730                 735

TAT GAA TTA AGA GGA TAT ATT GAA GAT AGT CAA GAT CTA GAG GTT TAT    2432
Tyr Glu Leu Arg Gly Tyr Ile Glu Asp Ser Gln Asp Leu Glu Val Tyr
740                 745                 750
```

FIG. 1G

```
TTA ATT CGT TAC AAT GCA AAA CAT GAA ACG CTA AAT GTT CCA GGT ACC    2480
Leu Ile Arg Tyr Asn Ala Lys His Glu Thr Leu Asn Val Pro Gly Thr
755                 760                 765

GAC TCC TTA CGG ACG CTT TCA GTT GAA AGC CAA AAC GGA AGG TGT GGA    2528
Asp Ser Leu Arg Thr Leu Ser Val Glu Ser Gln Asn Gly Arg Cys Gly
770                 775                 780

GAA CTG AAT CGA TGT ATG CCA CAT ATT AAA TGG AAT CCT GAT GTA GAT    2576
Glu Leu Asn Arg Cys Met Pro His Ile Lys Trp Asn Pro Asp Val Asp
785                 790                 795                 800

TGT TCC TGC AGA GAC GGA GAG AAG TGT GCC CAT CAT TCC CAT CAT TTC    2624
Cys Ser Cys Arg Asp Gly Glu Lys Cys Ala His His Ser His His Phe
        805                 810                 815

TCC CTA GAC ATT GAT GTT GGA TGC ACA GAC GAC TTG CAA GAG GAT TTA GGC    2672
Ser Leu Asp Ile Asp Val Gly Cys Thr Asp Leu Gln Glu Asp Leu Gly
820                 825                 830

GTG TGG GTT GTA TTC AAG ATT AAG ACG CAG GAA GGT TAT GCA AGA TTA    2720
Val Trp Val Val Phe Lys Ile Lys Thr Gln Glu Gly Tyr Ala Arg Leu
835                 840                 845

GGA AAT CTG GAA TTC ATC GAA GAG AAA CCA TTA GTA GGA GAA GCA CTG    2768
Gly Asn Leu Glu Phe Ile Glu Glu Lys Pro Leu Val Gly Glu Ala Leu
850                 855                 860

TCT CGT GTG AAG AGA GCG GAG GAC AAA AAA TGG AGA GAC AAA CGT GAA AAA    2816
Ser Arg Val Lys Arg Ala Glu Asp Lys Lys Trp Arg Asp Lys Arg Glu Lys
865                 870                 875                 880
```

FIG. 1H

```
TTG GAA TTG GAA ACA AAA CGA GTA TAT ACA GAG GCA AAA GAA GCT GTG        2864
Leu Glu Leu Glu Thr Lys Arg Val Tyr Thr Glu Ala Lys Glu Ala Val
                885                 890                 895

GAT GCT TTA TTC GTA GAT TCT CAA TAT GAT AGA TTA CAA GCA GAT ACA        2912
Asp Ala Leu Phe Val Asp Ser Gln Tyr Asp Arg Leu Gln Ala Asp Thr
            900                 905                 910

AAC ATT GGT ATG ATT CAT GCG GCA GAT AAA CTT GTT CAT CGA ATC TGC        2960
Asn Ile Gly Met Ile His Ala Ala Asp Lys Leu Val His Arg Ile Cys
        915                 920                 925

GAG ACT TAT CTT CCA GAA CTA CCT TTC ATT CCA GGA ATA AAC GCG ATA        3008
Glu Thr Tyr Leu Pro Glu Leu Pro Phe Ile Pro Gly Ile Asn Ala Ile
    930                 935                 940

ATT TTT GAA GAA TTA GAA GAA AAT CGT ATT TCC ACT GCA TTC TTC CTA TAC    3056
Ile Phe Glu Glu Leu Glu Glu Asn Arg Ile Ser Thr Ala Phe Phe Leu Tyr
945                 950                 955                 960

GAA GCA AGA AAT GTT ATT AAC AAT GGG GAT TTT AAT GGA TTA ACA            3104
Glu Ala Arg Asn Val Ile Asn Asn Gly Asp Phe Asn Gly Leu Thr
                965                 970                 975

TGC TGG AAC GTG AAA GGT CAT GTA GAT GTA CAA CAG AGC CAT CAT CGT        3152
Cys Trp Asn Val Lys Gly His Val Asp Val Gln Gln Ser His His Arg
            980                 985                 990

TCT GTC CTT GTT ATC CCA GAA TGG GAA GCA GAA GTG TCA CAA AAA GTT        3200
Ser Val Leu Val Ile Pro Glu Trp Glu Ala Glu Val Ser Gln Lys Val
        995                 1000                1005
```

FIG. 1J

```
GAA TTA GAA TAC TTC CCT GAA ACA GAT ACA GTA TGG ATT GAG ATT GGA     3632
Glu Leu Glu Tyr Phe Pro Glu Thr Asp Thr Val Trp Ile Glu Ile Gly
             1140                        1145                1150

GAA ACG GAA GGG AAG TTT ATT GTA GAC AGT GTC GAA TTA CTC CTT ATG     3680
Glu Thr Glu Gly Lys Phe Ile Val Asp Ser Val Glu Leu Leu Leu Met
         1155                    1160                    1165

GAA GAA TAGAATCCAA AAATAGTCGC TTAACCTCCG TTACAAATAA ATACGTAAAC      3736
Glu Glu
    1170

CGTTGTAGCA AAAAGAAAAA TGGACTTGTC                                    3766
```

BACILLUS THURINGIENSIS CRYET1 TOXIN GENE AND PROTEIN TOXIC TO LEPIDOPTERAN INSECTS

FIELD OF THE INVENTION

The present invention relates to a lepidopteran-toxic protein and the gene coding therefor. In particular, the present invention is directed to a gene designated as cryET1 (SEQ ID NO:1) and its protein designated as CryET1 (SEQ ID NO:2).

BACKGROUND OF THE INVENTION

B. thuringiensis (commonly known as B.t.) is a Gram-positive soil bacterium that often produces cellular inclusions during sporulation which are specifically toxic to certain orders and species of insects. Many different strains of B.t. have been shown to produce these inclusions of insecticidal crystal protein (ICP). Compositions including B.t. strains which produce insecticidal proteins have been commercially available and used as environmentally acceptable insecticides because they are quite toxic to the specific target insect, but are harmless to plants and other non-targeted organisms.

B. thuringiensis ICP toxins are active in the insect only after ingestion. After ingestion by an insect, the alkaline pH and proteolytic enzymes in the mid-gut solubilize the crystal allowing the release of the toxic components. These toxic components disrupt the mid-gut cells resulting in cessation of feeding and, eventually, death of the insect. B.t. has proven to be an effective and environmentally safe insecticide in dealing with various insect pests.

A number of genes encoding crystal proteins have been cloned from many strains of B.t. A good overview is set forth in H. Höfte and H. R. Whiteley, *Microbiol. Rev.*, 53, pp. 242–255 (1989), hereinafter "Höfte and Whiteley (1989)." This reference provides a good overview of the genes and proteins obtained from B.t. and their uses, adopts a nomenclature and classification scheme for B.t. genes and proteins, and has an extensive bibliography.

The nucleotide sequences of ICP genes responsible for a given crystal phenotype and active against the same insect order are generally more related than are the nucleotide sequences of B.t. genes encoding delta-endotoxin proteins active against different orders of insects. Höfte and Whiteley (1989) defines an ordered classification of genes encoding B.t. delta-endotoxin proteins based on homology of delta-endotoxin amino acid sequences, as well as similarities in insecticidal activity; a subranking has also been established based upon further refinement of sequence relationship. As noted by Höfte and Whiteley (1989), the majority of insecticidal B.t. strains are active against insects of the order Lepidoptera, i.e., caterpillar insects. Insecticidal crystal proteins specifically active against Lepidoptera have been designated CryI proteins. These ICPs are encoded by cryI genes. Other B.t. strains produce different classes of crystal proteins, e.g., CryII proteins are active against lepidopteran and (for CryIIA) dipteran insects; CryIII proteins are insecticidal to insects of the order Coleoptera, i.e., beetles; and CryIV proteins are active against insects of the order Diptera, i.e., flies and mosquitoes. A compilation of the amino acid identities for several CryI proteins as well as CryII, CryIII and CryIV proteins has been determined in Hodgman and Ellar, *J. DNA Sequencing and Mapping*, 1, pp. 97–106 (1990).

The CryI family of ICPs contains the largest number of known toxin genes derived from B.t., as evidenced by the survey in Höfte and Whiteley (1989) and by subsequent reports of CryI-type ICPs.

Schnepf et al., *J. Biol. Chem.*, 260, pp. 6264–6272 (1985), reported the complete nucleotide sequence for a toxin gene from B.t. kurstaki HD-1. This gene was subsequently classified as cryIA(a) by Höfte and Whiteley (1989). The published open reading frame extends 1176 amino acids and encodes a protein with a calculated molecular mass of 133,500 Daltons (Da). Another gene, also classified as cryIA(a), was isolated from B.t. subsp. kurstaki HD-1 Dipel ® by Shibano et al., *Gene* 34, pp. 243–251 (1985). As detailed in Table 2 of Höfte and Whiteley (1989), this gene is highly related, especially in the N terminal moiety, to cryIA(a) reported by Schnepf et al. (1985). CryIA(a) protein is broadly active against Lepidoptera; Höfte and Whiteley (1989) reports that four of five tested lepidopteran insects were sensitive to this toxin.

Other ICP genes subsequently identified as cryIA(a) that are greater than 99% identical to the holotype cryIA(a) gene have been identified in B. thuringiensis subspecies aizawai, (Shimizu et al., *Agric. Biol. Chem.* 52, pp. 1565–1573 (1988)), subspecies kurstaki, (Kondo et al., *Agric. Biol. Chem.* 51, pp. 455–463 (1987)), and subspecies entomocidus (Masson et al, *Nucleic Acids Res.* 17, p. 446 (1989)). The CryI-type nucleotide sequence disclosed in European Patent Application Publication No. 0 367 474, published May 9, 1990, of Mycogen Corporation, reveals a DNA sequence related to the cryIA(a) gene and its encoded protein that is 92% positionally identical to the holotype CryIA(a) ICP.

Wabiko et al., *DNA*, 5, pp. 305–314 (1986), describe the DNA sequence of an insecticidal toxin gene from B.t. subsp. berliner 1715, subsequently classified as cryIA(b) by Höfte and Whiteley (1989). The molecular mass of the protein encoded is 130,615 Da and sequential deletions indicate that the $NH_2$-terminal 612 amino acid polypeptide is toxic to lepidopteran insects. Höfte et al., *Eur. J. Biochem.*, 161, pp. 273–280 (1986), describe the cloning and nucleotide sequencing of a variant crystal protein gene from B.t. subsp. berliner 1715, subsequently also classified as cryIA(b). The cloned gene produces an approximately 130,000 Da protein which coincides with the mass of the major protein observed in the strain. The gene has an open reading frame of 3465 bases which would encode a protein 1155 amino acids in length having a mass of 130,533 Da. Similarities of this sequence to the previously reported sequences for the cloned crystal genes from B.t. kurstaki HD-1, B.t. kurstaki HD-73 and B.t. sotto are discussed in the Höfte et al. (1986) paper. Data identifying a minimal toxic fragment required for insecticidal activity are also presented. The cryIA(b) gene discussed in Höfte et al. (1986) differs in its deduced amino acid sequence by only two amino acids from the CryIA(b) protein reported by Wabiko et al.

Other cryIA(b) genes have been disclosed in Geiser et al., *Gene*, 48, pp. 109–118 (1986), Hefford et al., *J. Biotechnol.*, 6, pp. 307–322 (1987), Oeda et al., *Gene*, 53, pp. 113–119 (1987), Kondo et al., supra, Fischhoff et al., *Bio/Technology* 5, pp. 807–813, (1987) and Haider and Ellar, *Nucl. Acids Res.*, 16, p. 10927 (1988). Each of these six CryIA(b) ICPs is greater than 99% positionally identical to the holotype CryIA(b) toxin.

Adang et al., *Gene*, 36, pp. 289-300 (1985), report the cloning and complete nucleotide sequence of a crystal protein gene harbored on the 75 kilobase (kb) plasmid of strain B.t. subsp. kurstaki HD-73. The restriction map in the article identified this gene as holotype cryIA(c) under the current classification system of Höfte and Whiteley (1989). The complete sequence of the gene, spanning 3537 nucleotide base pairs (bp), coding for 1178 amino acids and potentially encoding a protein of 133,330 Da, is shown in the article. Toxicity data against *Manduca sexta* for the protein made by the CryIA(c) gene are also presented. CryIA(c) toxins have been isolated from several strains of B.t. subsp. kenyae that are highly related to the above-noted CryIA(c) toxin from B.t. subsp. kurstaki (greater than 99% positionally identical in deduced amino acid sequence) but whose protein products, although broadly active against lepidopteran insects, nonetheless show quantitatively different toxicities for individual insect species (Yon Tersch et al., *Appl. Environ. Microbiol.*, 57, pp. 349-358 (1991)).

Brizzard et al., *Nucleic Acids Res.*, 16, pp. 2723-2724 (1988), describe the nucleotide sequence of crystal protein gene cryA4 (subsequently classified as cryIB by Höfte and Whiteley (1989)) isolated from B.t. subsp. thuringiensis HD-2. Höfte and Whiteley (1989) report an insecticidal specificity of CryIB toxin for *Pieris brassicae*.

Honee et al., *Nucleic Acids Res.*, 16, p. 6240 (1988), describe the complete DNA sequence for the BTVI crystal protein gene isolated from B.t. subsp. entomocidus 60.5 (holotype CryIC by Höfte and Whiteley (1989)). This protein is reported to exhibit enhanced insecticidal activities against Spodoptera species.

Sanchis et al., *Mol. Microbiol.*, 3, pp. 229-238 (1989) report the nucleotide sequence for the N-terminal coding region (2470 nucleotides) and 5' flanking region of a gene from B.t. subsp. aizawai 7.29 now classified as the cryIC gene under the classification system of Höfte and Whiteley (1989). Sanchis et al. disclose similar information about the cryIC gene in European Patent Application Publication No. 0 295 156, published Dec. 14, 1988. The open reading frame encodes a truncated polypeptide 824 amino acids long with a calculated mass of 92,906 Da.

A gene isolated from B.t. subspecies aizawai and now classified as holotype cryID under the Höfte and Whiteley (1989) system is disclosed in European Patent Application Publication No. 0 358 557, published Mar. 14, 1990 of Plant Genetic Systems, N.V. Höfte and Whiteley (1989) report selective lepidopteran toxicity against *Manduca sexta* for the CryID protein, the CryID toxin being largely inactive against other lepidopteran insects tested.

The holotype cryIE gene, found in a B.t. subspecies darmstadiensis strain, is disclosed in European Patent Application Publication No. 0 358 557, supra. A highly related cryIE gene from B.t. subsp. kenyae is disclosed by Visser et al., *J. Bacteriol.* 172, pp. 6783-6788 (1990).

Visser et al., *Mol. Gen. Genet.*, 212, pp. 219-224 (1988) report the isolation and analysis of five toxin genes belonging to four different gene families from B.t. entomocidus 60.5, one of which is reported by Honee et al. (1988), Supra. Two of these genes, BTIV and BTVIII, are cryIA(a)-type genes according to the Höfte and Whiteley (1989) classification scheme. The BTVI gene, also reported by Honee et al. (1988) supra, is a cryIC gene according to the Höfte and Whiteley (1989) classification scheme. The authors state that the restriction map for another gene, designated BTV, closely resembles that identified for the cryID gene isolated from B.t. strain HD68 subsp. aizawai, and disclosed in European Patent Application Publication No. 0 358 557, supra. A fifth gene, designated BTVII, is also identified and its restriction map differs significantly from the other four genes described. Toxicity data against several lepidopteran insects, *S. exigua, S. littoralis, H. virescens* and *P. brassicae*, are presented for each of the isolates. The BTV gene product was inactive against all insects tested. The BTVI protein is highly active against Spodoptera larvae, and the BTVII protein is toxic to *P. brassicae*.

Additional genes within the cryI family have been reported in the literature. A gene found in B.t. subsp. aizawai and described as cryIF is disclosed by Chambers et al. in *J. Bacteriol.*, 173, pp. 3966-3976 (1991) and in PCT International Publication No. WO91/16434, published Oct. 31, 1991. A gene described as cryIG from B.t. subsp. galleria is disclosed by Smulevitch et al., *FEBS Lett.*, 293, pp. 25-28 (1991). A gene that is highly related to the cryIG gene has been isolated from B.t. DSIR 517 by Gleave et al., *J. Gen. Microbiol.*, 138, pp. 55-62 (1992).

A novel gene related to cryI-type genes is disclosed in PCT International Publication No. WO 90/13651, published Nov. 15, 1990, of Imperial Chemical Industries PLC. This gene encodes an 81 kDa polypeptide (Cry pJH11) that is broadly insecticidal and more distantly related to the family of cryI sequences than are most other reported cryI-type sequences. Four CryI-type sequences are disclosed in European Patent Application Publication No. 0 405 810, published Jan. 2, 1991, of Mycogen Corporation. Inspection of the cryI-type sequences revealed that one of the disclosed genes (cry 81IB2) belongs to the cryIC class, one (cry 81IB) belongs to the cryID class, and one (cry 81IA) belongs to the CryIF class. The fourth disclosed cryI sequence (cry 81IA2) appears to belong to a new class. Two cryI sequences are disclosed in European Patent Application Publication No. 0 401 979, published Dec. 12, 1990, of Mycogen Corporation. One of the disclosed sequences (PS82A2) appears to encode a novel gene, the other sequence (PS82RR) is highly related to the novel sequence cry 81IA2 disclosed in European Patent Application Publication No. 0 405 810.

Five novel cry sequences are disclosed in European Patent Application Publication No. 0 462 721, published Dec. 27, 1991, of Mycogen Corporation. These Cry proteins are reported to be nematocidal.

SUMMARY OF THE INVENTION

Briefly stated, the present invention relates to a purified and isolated cryET1 gene having a nucleotide base sequence coding for the amino acid sequence (SEQ ID NO:2) illustrated in FIG. 1.

The purified and isolated cryET1 gene may have a coding region extending from nucleotide bases 177 to 3689 (including the stop codon) in the nucleotide base sequence illustrated in FIG. 1 (SEQ ID NO:1).

The present invention also relates to the CryET1 protein which is obtainable from the CryET1 gene and which is insecticidal to lepidopteran insects and, in particular, to *Plutella xylostella* (diamondback moth).

Additionally, the present invention relates to a biologically pure culture of a *Bacillus thuringiensis* bacterium designated as strain EG7094 transformed with a cryET1 gene having a coding region (SEQ ID NO:1) illustrated in FIG. 1, or mutants thereof having insecticidal activity against lepidopteran insects.

The invention also relates to a biologically pure culture of a *Bacillus thuringiensis* bacterium designated as strain EG5092, or mutants thereof having insecticidal activity against lepidopteran insects. B.t. strain EG5092 is a wild type isolate and is the B.t. strain from which the cryET1 gene was isolated.

Additional aspects of the present invention relate to recombinant plasmids containing the cryET1 gene; bacteria transformed with the recombinant plasmid; insecticide compositions comprising the protein and/or the transformed bacterium and/or other bacteria containing the CryET1 protein, with an agriculturally acceptable carrier; a method of controlling lepidopteran insects using the insecticide; plants transformed with the cryET1 gene; and hybridization probes containing the cryET1 gene wherein the gene or a portion of it is labeled for such use.

BRIEF DESCRIPTION OF THE DRAWINGS

FIG. 1 comprises FIGS. 1A through 1J and shows the nucleotide sequence of the cryET1 gene (SEQ ID NO:1) and the deduced amino acid sequence of the CryET1 protein (SEQ ID NO:2).

DETAILED DESCRIPTION OF THE PREFERRED EMBODIMENTS

Figure 2:
FIG. 2 is a photograph of an ethidium bromide stained agarose gel containing size-fractionated plasmids of B.t. strain EG5092, with plasmid sizes in megadaltons (MDa) being shown.

A novel *Bacillus thuringiensis* (B.t.) toxin gene cryET1 was obtained from a novel B.t. isolate designated EG5092. Isolation of B.t. strain EG5092, isolation of the novel toxin gene cryET1, construction of a Bacillus/*E. coli* shuttle vector containing cryET1 (pEG744) and transformation of pEG744 into a B.t. host (B.t. strain EG7566) to produce a recombinant B.t. EG7094 expressing the cryET1 gene product, a toxin protein designated as CryET1, are described generally in the Examples.

Subcultures of B.t. EG5092 and B.t. EG7094 were deposited in the permanent collection of the Agricultural Research Service Culture Collection, Northern Regional Research Laboratory (NRRL), U.S. Department of Agriculture, 1815 North University Street, Peoria, Ill. 61604, U.S.A. The accession numbers and deposit dates are as follows:

| Subculture | Accession No. | Deposit Date |
|---|---|---|
| B.t. EG5092 | NRRL B-18973 | May 4, 1992 |
| B.t. EG7094 | NRRL B-18972 | May 4, 1992 |
| B.t. HD73-26 | NRRL B-18508 | June 20, 1989 |

These microorganism deposits were made under the provisions of the "Budapest Treaty on the International Recognition of the Deposit of Microorganism for the Purposes of Patent Procedure." All restrictions on the availability to the public of these deposited microorganisms will be irrevocably removed upon issuance of a United States patent based on this application.

The present invention is intended to cover mutants and recombinant or genetically engineered derivatives, e.g., truncated versions, of the CryET1 gene (SEQ ID NO:1) shown in FIG. 1 that yield a protein with insecticidal properties essentially the same as those of the CryET1 protein (SEQ ID NO:2), also shown in FIG. 1. Likewise, the present invention covers those gene nucleotide base sequences that encode the amino acid sequence (SEQ ID NO:2) of the CryET1 protein. Variations may be made in the cryET1 gene nucleotide base sequence (SEQ ID NO:1) which do not affect the amino acid sequence of the gene product, since the degeneracy of the genetic code is well known to those skilled in the art. Moreover, there may be some variations or truncations in the coding regions of the cryET1 nucleotide base sequence which allow expression of the gene and production of functionally equivalent forms of the CryET1 insecticidal protein. These variations or truncations, which can be determined without undue experimentation by those of ordinary skill in the art with reference to the present specification, are to be considered within the scope of the appended claims, since they are fully equivalent to the specifically claimed subject matter.

It has been shown that proteins of identical structure and function may be constructed by changing the amino acid sequence, if such changes do not alter the protein secondary structure (Kaiser and Kezdy, *Science*, 223, pp. 249–255 (1984)). Single amino acid substitutions have been introduced by site-directed mutagenesis at various positions of CryIA(a) toxin protein without altering the insecticidal properties of the parent toxin (Ge et al., *Proc. Natl. Acad. Sci. USA*, 86, pp. 4037–4041 (1989)). The present invention includes mutants of the amino acid sequences disclosed herein which have an unaltered protein secondary structure or, if the structure is altered, where the mutant has the substantially equivalent biological activity retained.

The cryET1 gene (SEQ ID NO:1) is also useful as a DNA hybridization probe, for discovering similar or closely related cryET1-type genes in other B.t. strains. The cryET1 gene (SEQ ID NO:1), or portions or derivatives thereof, can be labeled for use as a hybridization probe, e.g., with a radioactive label, using conventional procedures.

The cryET1 gene (SEQ ID NO:1) and the corresponding insecticidal CryET1 protein (SEQ ID NO:2) were first identified in B.t. strain EG5092, a novel B.t. isolate. The characteristics of B.t. strain EG5092 are more fully described in the Examples.

The Bacillus strains described herein may be cultured using conventional growth media and standard fermentation techniques. The B.t. strains harboring the cryET1 gene (SEQ ID NO:1) may be fermented, as described in Example 1, until the cultured B.t. cells reach the stage of their growth cycle when CryET1 crystal protein (SEQ ID NO:2) is formed. For sporogenous B.t. strains, fermentation is typically continued through the sporulation stage when the CryET1 crystal protein is formed along with spores. The B.t. fermentation culture is then typically harvested by centrifugation, filtration or the like to separate fermentation culture solids containing the CryET1 crystal protein from the culture medium.

The separated fermentation solids are primarily CryET1 crystal protein (SEQ ID NO:2) and B.t. spores (if a sporulating host is employed), along with some cell debris, some intact cells, and residual fermentation medium solids. If desired, the crystal protein may be separated from the other recovered solids via conventional methods, e.g., density gradient fractionation.

The B.t. strains exemplified in this disclosure are sporulating varieties (spore forming or sporogenous strains) but the cryET1 gene (SEQ ID NO:1) also has utility in asporogenous Bacillus strains, i.e., strains that produce the crystal protein without production of spores. It should be understood that references to "fermentation cultures" of B.t. strains containing the cryET1 gene (SEQ ID NO:1) in this disclosure are intended to cover sporulated B.t. cultures, i.e., B.t. cultures containing the CryET1 crystal protein and spores, and sporogenous Bacillus strains that have produced crystal proteins during the vegetative stage, as well as asporogenous Bacillus strains containing the cryET1 gene (SEQ ID NO:1) in which the culture has reached the growth stage where the crystal protein is actually produced.

Mutants of B.t. strains harboring the cryET1 gene (SEQ ID NO:1) can be made by procedures well known in the art. For example, an asporogenous mutant can be obtained through ethylmethane sulfonate mutagenesis. Mutants can also be made using ultraviolet light and nitrosoguanidine by procedures that are well known to those skilled in the art. References in this specification to "mutants" of wild-type or recombinant B.t. strains harboring the cryET1 gene refer to those derivatives which are capable of producing a toxin protein exhibiting insecticidal activity against lepidopteran insects.

The CryET1 protein (SEQ ID NO:2) is an insecticidal compound active against lepidopteran insects, particularly *Plutella xylostella* (diamondback moth). The CryET1 protein (SEQ ID NO:2) may be used as the active ingredient in insecticidal formulations useful for controlling lepidopteran insects such as the diamondback moth. Such insecticidal formulations or compositions typically contain agriculturally acceptable carriers or adjuvants in addition to the active ingredient and are prepared and used in a manner well known to those skilled in the art.

The CryET1 protein (SEQ ID NO:2) may be employed in insecticidal formulations in isolated or purified form, e.g., as the crystal protein itself. Alternatively, the CryET1 protein (SEQ ID NO:2) may be present in the recovered fermentation solids, obtained from culturing of a Bacillus strain, e.g., *Bacillus thuringiensis*, or other microorganism host carrying the cryET1 gene (SEQ ID NO:1) and capable of producing the CryET1 protein. The recovered fermentation solids containing the CryET1 protein may be dried, if desired, prior to incorporation in the insecticidal formulation. Preferred Bacillus hosts include B.t. strain EG7566, a plasmid-free strain lacking crystal toxin proteins (Cry−), described in Example 2. Genetically engineered or transformed B.t. strains or other host microorganisms containing a recombinant plasmid that expresses the cloned cryET1 gene (SEQ ID NO:1), obtained by recombinant DNA procedures, may also be used.

The formulations or compositions of this invention containing the insecticidal CryET1 protein (SEQ ID NO:2) as the active component are applied at an insecticidally effective amount which will vary depending on such factors as, for example, the specific lepidopteran insects to be controlled, the specific plant or crop to be treated and the method of applying the insecticidally active compositions.

The insecticide compositions are made by formulating the insecticidally active component with the desired agriculturally acceptable carrier. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally acceptable carrier" covers all adjuvants, e.g., inert components, dispersants, surfactants, tackifiers, binders, etc. that are ordinarily used in insecticide formulation technology; these are well known to those skilled in insecticide formulation.

The formulations containing the CryET1 protein (SEQ ID NO:2) and one or more solid or liquid adjuvants are prepared in known manners, e.g., by homogeneously mixing, blending and/or grinding the insecticidally active CryET1 protein component with suitable adjuvants using conventional formulation techniques.

The insecticidal compositions of this invention are applied to the environment of the target lepidopteran insect, typically onto the foliage of the plant or crop to be protected, by conventional methods, preferably by spraying. Other application techniques, e.g., dusting, sprinkling, soaking, soil injection, seed coating, seedling coating or spraying, or the like, are also feasible and may be required for insects that cause root or stalk infestation. These application procedures are well known in the art.

The cryET1 gene (SEQ ID NO:1) may be introduced into a variety of microorganism hosts, using procedures well known to those skilled in the art for transforming suitable hosts under conditions which allow for stable maintenance and expression of the cloned cryET1 gene. Suitable hosts that allow the CryET1 gene (SEQ ID NO:1) to be expressed and the CryET1 protein (SEQ ID NO:2) to be produced include B.t. and other Bacillus species such as *B. subtilis* or *B. megaterium*. Genetically altered or engineered microorganisms containing the cryET1 gene (SEQ ID NO:1) can also contain other toxin genes present in the same microorganism; these genes could concurrently produce ICPs different from the CryET1 protein.

Plant-colonizing or root-colonizing microorganisms may also be employed as the host for the cryET1 gene (SEQ ID NO:1). Various procedures well known to those skilled in the art are available for introducing the cryET1 gene (SEQ ID NO:1) into the microorganism host under conditions which allow for stable maintenance and expression of the gene in the resulting transformants.

The transformants, i.e., host microorganisms that harbor a cloned gene in a recombinant plasmid, can be isolated in accordance with conventional methods, usually employing a selection technique, which allows growth of only those host microorganisms that contain a recombinant plasmid. The transformants then can be tested for insecticidal activity. These techniques are standard procedures well known to those skilled in the art.

Characteristics of particular interest in selecting a host cell for purposes of production include ease of introducing the gene into the host, availability of expression systems, efficiency of expression, stability of the CryET1 insecticidal protein in the host, and the presence of auxiliary genetic capabilities. The cellular host containing the insecticidal cryET1 gene (SEQ ID NO:1) may be grown in any convenient nutrient medium, where expression of the cryET1 gene is obtained and CryET1 protein (SEQ ID NO:2) produced, typically to sporulation. The sporulated cells containing the crystal protein may then be harvested in accordance with conventional methods, e.g., centrifugation or filtration.

The cryET1 gene (SEQ ID NO:1), particularly the toxin portion (N-terminal moiety) thereof, may also be incorporated into a plant which is capable of expressing the gene and producing CryET1 protein (SEQ ID NO:2), rendering the plant more resistant to insect attack. Genetic engineering of plants with the cryET1 gene (SEQ ID NO:1) may be accomplished by introducing the desired DNA containing the gene into plant tissues or cells, using DNA molecules of a variety of forms and origins that are well known to those skilled in plant genetic engineering. Examples of techniques for introducing DNA into plant tissue are disclosed in European Patent Application Publication No. 0 289 479, published Nov. 1, 1988, of Monsanto Company and by Perlak et al. in "Modification of the Coding Sequence Enhances Plant Expression of Insect Control Protein Genes," *Proc. Natl. Acad. Sci. USA*, 88, pp 3324–3328 (1991).

DNA containing the cryET1 gene (SEQ ID NO:1) or a modified CryET1 gene capable of producing the CryET1 protein (SEQ ID NO:2) may be delivered into the plant cells or tissues directly by infectious plasmids, such as Ti, the plasmid from *Agrobacterium tumefaciens*, viruses or microorganisms like *A. tumefaciens*. Additionally, the use of lysosomes or liposomes, microinjection by mechanical methods and by other techniques familiar to those skilled in plant genetic engineering may be used.

The characteristics of the CryET1 protein (SEQ ID NO:2), sequencing of the cryET1 gene (SEQ ID NO:1), comparison of sequence data to known B.t. toxin genes and insecticidal activity of B.t. EG7094 and the CryET1 protein are described in the following specific, non-limiting examples.

EXAMPLE 1

Characterization of B.t. EG5092 and B.t. EG7094

B.t. strain EG5092 is a wild-type isolate, identified by visual examination of the colony as exhibiting a unique crystal morphology, and was isolated as a colony from maize dust. The colony contained endospores and bipyramidal, apparently "jagged" crystalline inclusions. Subsequent insect bioassay of this wild-type B.t. strain confirmed its insecticidal activity towards lepidopteran insects.

The complement of native plasmids contained within isolated B.t. EG5092 was determined by modified Eckhardt agarose gel electrophoresis as described by Yon Tersch et al., in *Appl. Environ. Microbiol.*, 57, pp. 349–358 (1991). The results, as shown in FIG. 2, revealed the presence of 4.9, 6.4, 8.7, 49, 59, 98 and 115 MDa plasmids. This pattern of native plasmids did not correspond to patterns typical of known serovars (Carlton and Gonzalez, pp. 246–252, in *Molecular Biology of Microbial Differentiation*, J. A. Hoch and P. Setlow, ed., American society for Microbiology, Washington, D.C. (1985).

Wild-type B.t. strain EG5092 was grown 5 days at 25° C. on Luria plates (10 g/l tryptone, 5 g/l yeast extract, 5 g/l NaCl, 15 g/l agar). Recombinant B.t. strain EG7094, containing the cryET1 gene, was likewise grown on Luria plates, but containing 10 μg of tetracycline per ml. Cells were recovered from the surfaces of the plates. B.t. strain EG5092 was observed to have fully lysed naturally. The partially lysed culture of B.t. strain EG7094 was fully lysed by repeated intermittent agitation with 0.1 mm zirconium beads. Both cultures were washed two times with high salt TNT buffer (50 mM Tris HCl pH 7.5, 1.0M NaCl, 0.05% Triton® X-100) followed by two washes with TNT buffer (50 mM Tris HCl pH 7.5, 100 mM NaCl, 0.05% Triton® X-100). Aliquots of the washed crystals were solubilized by heating in Laemmli buffer (10% (w/w) glycerol, 5% (w/w) 2-mercaptoethanol, 1% (w/v) SDS, 0.188M Tris HCl pH 6.8, 0.01% (v/v) bromphenol blue) at 100° C. for 5 minutes. The solubilized crystal proteins were size fractionated by SDS-PAGE. After size fractionation, the proteins were visualized by staining with Coomassie Blue R-250 dye.

Figure 3:
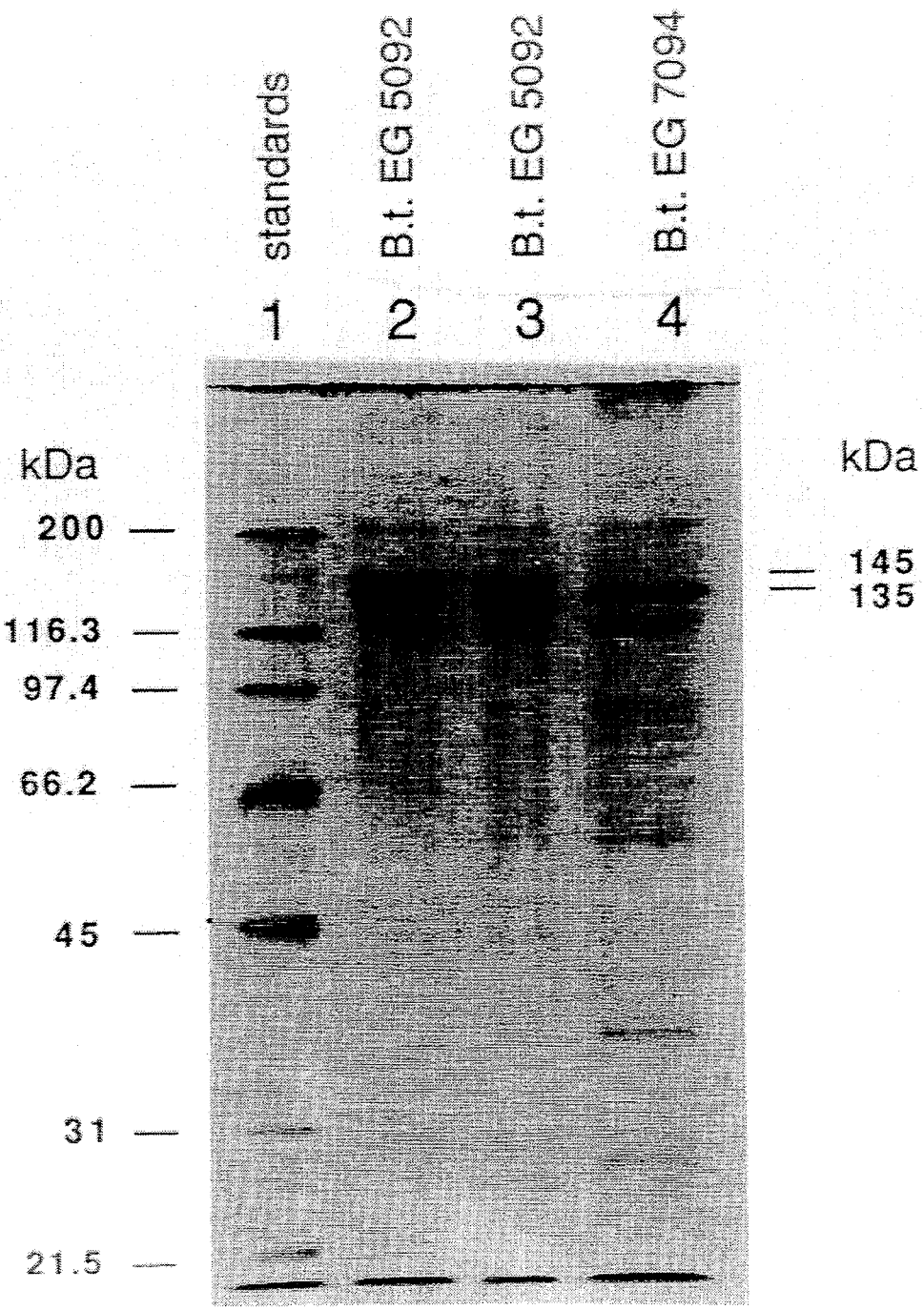
FIG. 3 is a photograph of a Coomassie blue stained gel containing size-fractionated proteins from B.t. strains EG5092 and EG7094, obtained by sodium dodecyl sulfate polyacrylamide gel electrophoresis (SDS-PAGE).

FIG. 3 shows the results of these protein size fractionation analyses where lane 1 is a molecular mass size standard, lanes 2 and 3 are duplicate runs of B.t. strain EG5092 and lane 4 is B.t. strain EG7094. The numbers on the right side indicate the apparent molecular masses, in kilodaltons (kDa), of the crystal proteins synthesized by B.t. strains EG5092 and EG7094. As shown in lane 4 for EG7094, a major protein having an apparent molecular mass estimated to be approximately 135,000 Da was solubilized from centrifuged fermentation solids containing B.t. strain EG7094 spores and crystals. B.t. EG5092, as shown in lanes 2 and 3, exhibited two major proteins whose apparent molecular masses were estimated to be about 145,000 and about 135,000 Da.

EXAMPLE 2

Cloning of the cryET1 Gene

Figure 4:
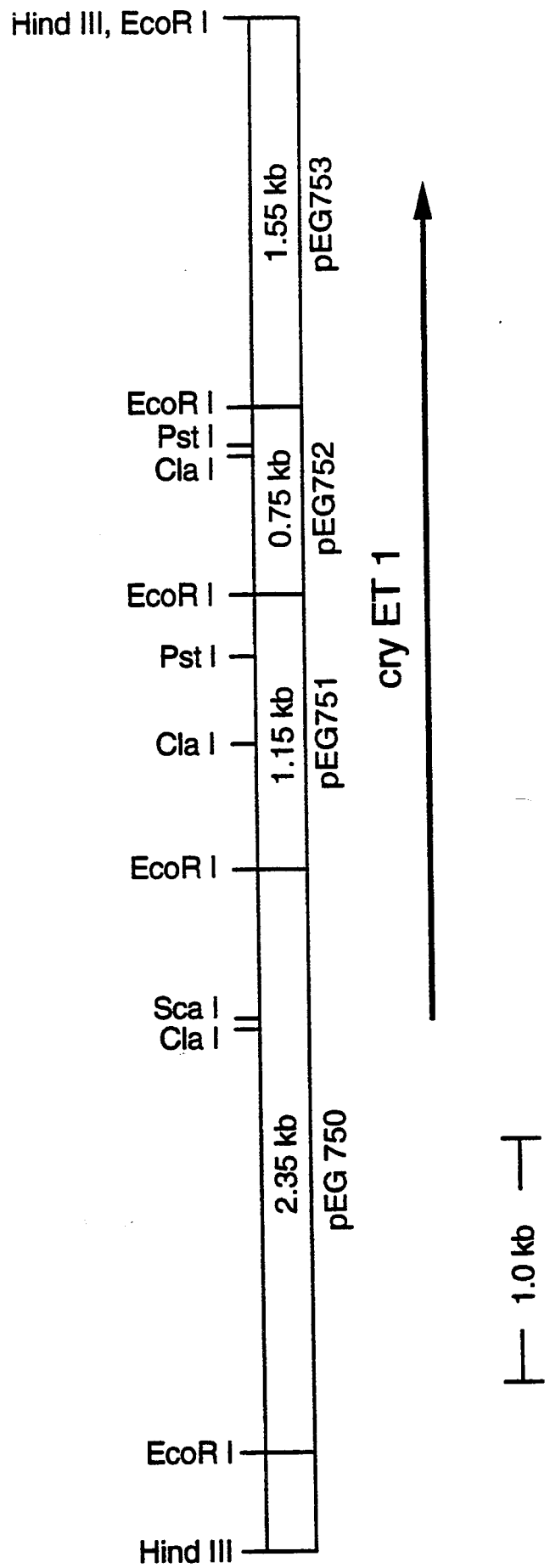
FIG. 4 is a restriction map of the 6.3 kb HindIII fragment of plasmid pEG744 and of four EcoRI fragments utilized in the cloning of plasmids pEG750, pEG751, pEG752 and pEG753. The location and orientation of the cryET1 gene are indicated by the arrow.

Genomic DNA was isolated from B.t. strain EG5092 and then digested with HindIII. Resulting fragments of approximately 4–8 kilobase pairs (kb) in size were purified by gel electrophoresis and electroelution. These fragments were ligated to *E. coli* and Bacillus vector pEG147 (described by Yon Tersch et al., *Appl. Environ. Microbiol.*, 57, pp. 349–358 (1991)), and the ligation mixture was then used to transform *E. coli*. Colony hybridization to a cryI-type gene probe (the cryIA(b) gene was used) identified positive colonies. One colony containing a recombinant plasmid designated pEG744 was selected for further analysis. HindIII digestion of pEG744 revealed an insert fragment 6.3 kb in size, whose restriction map is shown in FIG. 4. Plasmid pEG744 was transformed into B.t. strain EG7566; B.t. strain EG7566 is a plasmid-free strain obtained by curing B.t. strain HD73-26, to eliminate this latter strain's single, 4.9 MDa plasmid. The resulting strain was designated B.t. strain EG7094, and this strain contained the cryET1 gene as its sole B.t. toxin gene.

EXAMPLE 3

Sequencing of the cryET1 Gene

Plasmid pEG744 (Example 2) was digested with EcoRI, and four of the five generated fragments were cloned separately into pUC18. The four plasmids were designated pEG750, pEG751, pEG752 and pEG753. Mapping of the EcoRI fragment inserts in each of these plasmids is also shown in FIG. 4. DNA sequences were determined for the entire EcoRI fragments cloned in pEG751 and pEG752 and for parts of the EcoRI fragments cloned in pEG750 and pEG753. The DNA sequences were joined at the EcoRI junctions to give a continuous sequence of 3766 nucleotides which is shown in FIG. 1. Inspection of the sequence revealed an open reading frame beginning at position 177 and extending to position 3689 (including the stop codon). The deduced 1170 amino acid sequence of the gene product is also shown in FIG. 1. The gene has been designated cryET1. The mass of the CryET1 protein (SEQ ID NO:2) encoded by the cryET1 gene (SEQ ID NO: 1), as deduced from the open reading frame, is 33,566 Da.

EXAMPLE 4

Homology of CryET1 to Other Insecticidal Crystal Proteins

The deduced amino acid sequence of the protein product of the cryET1 gene was compared to a database of holotype and other known B.t. toxin protein amino acid sequences. The results shown in Table 1 indicate that CryET1 is a novel ICP different from all previously described ICPs. The amino acid sequence homologies show that the protein product of the cryET1 gene is most closely related to the CryI class of ICP gene products. Most CryI toxins showed between 60 and 66% amino acid identity to CryET1 in pairwise alignments of the complete protoxin amino acid sequence. Alignments limited to the N-terminal toxic fragments showed lower percent identities, which is consistent with the generally higher conservation of C-terminal sequence among the family of CryI toxins. Alignments limited to the N-terminal toxic fragment of CryET1 showed lesser homologies to CryII, CryIII and CryIV ICPs.

CryET1 amino acid sequence divergences from the family of ICP sequences imply corresponding divergences in the nucleotide sequences of the corresponding genes.

TABLE 1

Sequence Identities of CryET1 ICP to Other B.t. ICP Toxins

| ICP Toxin | Percent amino acid sequence identity[1] to CryET1 protoxin | toxic moiety | ICP Sequence Reference |
|---|---|---|---|
| CryIA(a) | 66 | 52 | Schnepf et al., J. Biol. Chem., 260, pp. 6264–6272 (1985) |
| CryIA(b) | 65 | 52 | Wabiko et al., DNA, 5, pp. 305–314 (1986) |
| CryIA(c) | 63 | 49 | Adang et al., Gene, 36, pp. 289–300 (1985) |
| CryIB | 62 | 42 | Brizzard and Whiteley Nucleic Acids Res., 16, pp. 2723–2724 (1988) |
| CryIC | 65 | 50 | Honee et al., Nucleic Acids Res., 16, p. 6240 (1988) |
| CryID | 64 | 48 | European Pat. Appln. Publ. No. 0 358 557, publ. March 14, 1990 of Plant Genetic Systems |
| CryIE | 63 | 45 | European Patent Appln. Publ. No. 0 358 557, publ. March 14, 1990 of Plant Genetic Systems |
| CryIF | 64 | 49 | Chambers et al., J. Bacteriol., 173, pp. 3966–3976 (1991) and European Patent Appln. Publ. No. 0 405 810, (Cry 8IIA) publ. January 2, 1991 of Mycogen Corp. |
| CryIG | 34 | 31 | Smulevitch et al., FEBS Lett., 293, pp. 25–28 (1991) |
| Cry 8IIA2 | 65 | 50 | European Patent Appln. Publ. No. 0 405 810, publ. January 2, 1991 of Mycogen Corp. |
| Cry PS81A2 | 65 | 44 | European Patent Appln. Publ. No. 0 401 979, publ. December 12, 1990 of Mycogen Corp. |
| Cry pJH11 | | 38 | Patent Cooperation Treaty WO 90/13651, publ. November 15, 1990 of Imperial Chemical Industries PLC |
| CryIIA | | 26 | Donovan et al., J. Biol. Chem., 263, pp. 561–567 (1988) (Erratum J. Biol. Chem., 264, p. 4740 (1989)) |
| CryIIIA | | 36 | Herrnstadt et al., Gene, 57, pp. 37–46 (1987) |
| CryIVA | 33 | 30 | Ward and Ellar, Nucleic Acids Res., 15, p. 7195 (1987) |
| Cry PS17A | 20 | 24 | European Patent Appln. Publ. No. 0 462 721, published December 27, 1991 of Mycogen Corp. |
| Cry PS17B | 26 | 25 | European Patent Appln. Publ. No. 0 462 721, published December 27, 1991 of Mycogen Corp. |
| Cry PS33F | 24 | 23 | European Patent Appln. Publ. No. 0 462 721, published December 27, 1991 of Mycogen Corp. |
| Cry PS52A1 | | 17 | European Patent Appln. Publ. No. 0 462 721, published December 27, 1991 of Mycogen Corp. |
| Cry PS69D1 | | 19 | European Patent Appln. Publ. No. 0 462 721, published December 27, |

TABLE 1-continued

Sequence Identities of CryET1 ICP to Other B.t. ICP Toxins

| ICP Toxin | Percent amino acid sequence identity[1] to CryET1 | | ICP Sequence Reference |
|---|---|---|---|
| | protoxin | toxic moiety | |
| | | | 1991 of Mycogen Corp. |

[1]Percent identity equals the number of matched amino acids divided by the total number of positions in the alignment for each pair wise comparison. Alignments of toxic moieties were limited to the N-terminal fragments (complete proteins for CryIIA and CryIIIA) that aligned best to the N-terminal 604 amino acids of CryET1.

EXAMPLE 5

Insecticidal Activity of CryET1 Protein

Insecticidal activities of solubilized CryET1 toxin from a culture of recombinant B.t. strain EG7094 containing the cryET1 gene were determined at a single toxin dose level against a diluent control after solubilization of crystalline inclusions in base and elimination of non-soluble spores and cell debris by centrifugation. A Luria broth culture of B.t. strain EG7094 containing crystal toxin proteins was solubilized by addition of NaOH to 0.1N. After 5 minutes at room temperature, spores and cell debris were removed by centrifugation. Solubilized toxin was diluted 1:5 with 0.005% Triton ® X-100, then 50 µl aliquots were applied to the surfaces of 32 wells (1.8 cm² surface area) containing insect diet and dried for 1 hour at 30° C. A general purpose Noctuidae artificial diet as described by E. G. King et al. in *Handbook of Insect Rearing*, Vol. 2, P. Singh and R. F. Moore (eds.), pp. 323–328, Elsevier Science Publishers B.V., Amsterdam (1985) was used for *Trichoplusia ni*, *Ostrinia nubilalis* and *Heliothis virescens*. Other standard diets were used for the other lepidopteran insects tested. One neonate larva (third-instar larvae in the case of *P. xylostella*) was added to each cup, and the cups were incubated at 30° C. Mortality was recorded after seven days.

TABLE 2

Bioassay Activities of Solubilized CryET1

| Solubilized toxin | % mortality | | | | | | | | |
|---|---|---|---|---|---|---|---|---|---|
| | Ag | Ai | Hv | On | Px | Pi | Se | Tn | Ld | Duh |
| EG7094 | 6.3 | 0 | 6.3 | 19 | 100 | 94 | 3.1 | 66 | 0 | 16 |
| diluent control | 3.3 | 6.3 | 1.6 | 4.7 | 6.3 | 0 | 1.6 | 1.6 | 3 | 13 |

Ag: *Anticarsia gemmatalis* - Velvetbean Caterpillar
Ai: *Agrotis ipsilon* - Black Cutworm
Hv: *Heliothis virescens* - Tobacco Budworm
On: *Ostrinia nubilalis* - European Corn Borer
Px: *Plutella xylostella* - Diamondback Moth
Pi: *Pseudoplusia includens* - Soybean Looper
Se: *Spodoptera exigua* - Beet Armyworm
Tn: *Trichoplusia ni* - Cabbage Looper
Ld: *Leptinotarsa decemlineata* - Colorado Potato Beetle
Duh: *Diabrotica undecimpunctata howardi* - Southern Corn Rootworm The results (Table 2) indicate that diamondback moth, soybean looper, and to a lesser extent, cabbage looper were sensitive to the solubilized CryET1 protein (SEQ ID NO:2), i.e., these lepidopteran insects were readily killed at the dose levels of CryET1 protein tested. Other insects such as tobacco budworm and European corn borer that are usually sensitive to other known CryI toxins were either not sensitive or only slightly sensitive to the CryET1 toxin protein at the dose levels tested.

In a separate procedure, to illustrate the dose response of CryET1 toxin against various lepidopteran insect larvae, crystal inclusions from B.t. strain EG7094 cultures were first separated from spores and cell debris by equilibrium centrifugation on Renografin-76 gradients by the method of P.C. Fitz-James et al in *J. Invertebr. Pathol.* 43, pp. 47–58 (1984). The amount of CryET1 protoxin recovered from the gradients was quantified by laser densitometry after solubilization of the recovered crystal protein with base and a reducing agent.

Dilutions of purified CryET1 crystals were prepared in 0.005% Triton ® X-100. Aliquots of appropriate dilutions (150 µl) were applied to the surfaces of 32 wells and assayed as indicated above. Control assays of CryIA(b) and CryIA(c) crystals were included. The results are shown in the following Table 3.

TABLE 3

Insecticidal Activities of CryIA(b), CryIA(c) and CryET1 Crystals Against Lepidopteran Insects

| ICP | Dose/ ng/well | % mortality | | | | | |
|---|---|---|---|---|---|---|---|
| | | Hv | On | Px | Pi | Se | Tn |
| CryIA(b) | 10,000 | 100 | 100 | N.D. | 100 | 78 | 100 |
| | 1,000 | 100 | 100 | 100 | 100 | 0 | 97 |
| | 100 | 97 | 94 | 97 | 84 | 0 | 0 |
| | 10 | N.D. | N.D. | 97 | N.D. | N.D. | N.D. |
| CryIA(c) | 10,000 | N.D. | N.D. | N.D. | N.D. | 3 | 100 |
| | 1,000 | 100 | 100 | 100 | 88 | 0 | 100 |
| | 100 | 100 | 100 | 100 | 100 | 0 | 91 |
| | 10 | 100 | 69 | 94 | N.D. | N.D. | N.D. |
| CryET1 | 10,000 | 0 | 9 | 100 | 47 | 0 | 22 |
| | 1,000 | 6 | 16 | 100 | 9 | 0 | 6 |
| | 100 | 0 | 9 | 38 | 6 | 0 | 6 |

Hv: *Heliothis virescens* - Tobacco Budworm
On: *Ostrinia nubilalis* - European Corn Borer
Px: *Plutella xylostella* - Diamondback Moth
Pi: *Pseudoplusia includens* - Soybean Looper
Se: *Spodoptera exigua* - Beet Armyworm
Tn: *Trichoplusia ni* - Cabbage Looper
N.D. - Not determined.

The results indicate the same spectrum of activity as was observed in the assays of solubilized CryET1 (Table 2). CryET1 protein (SEQ ID NO:2) shows a specificity of activity unlike that of any other CryI toxin. The CryET1 toxin protein was shown to be insecticidal to diamondback moth, soybean looper and cabbage looper. Diamondback moth was observed to be the most sensitive. The activity observed for CryET1 protein appeared to be selective for diamondback moth, and Example 6 describes additional work performed to determine the LC$_{50}$ value for CryET1 against this insect. Insecticidal activity observed against the other lepidopteran insects tested was decreased relative to activity exhibited by CryIA(b) and CryIA(c).

EXAMPLE 6

Bioassay of CryET1 Crystals Against Diamondback Moth

The insecticidal activity of CryET1 protein was determined against larvae of *Plutella xylostella* (diamondback moth), an insect pest that causes significant damage to vegetables, particularly cold crops. In this procedure, the LC$_{50}$ value of CryET1 was measured against *P. xylostella* larvae, the LC$_{50}$ dose being that which killed half of the insects tested, i.e., the median lethal concentration.

Crystal inclusions from a B.t. strain EG7094 culture were first separated from spores and cell debris by equilibrium centrifugation on Renografin-76 gradients, as described in Example 5. The amount of recovered CryET1 protoxin was then quantified by a commercial dye binding assay after solubilization of the crystals with base and a reducing agent.

To quantify the insecticidal activity, dilutions of purified CryET1 crystals were prepared in 0.005% Triton ® X-100. Aliquots of eight two-fold serial dilutions (50 µl) were applied to the surfaces of 32 wells, one *P. xylostella* larva was placed in each well, and the bioassay was performed as indicated in Example 5.

Composite results for two such bioassays showed an LC$_{50}$ value of 354 ng/well for CryET1 crystals against diamondback moth (95% confidence intervals were 311–403 ng/well ).

The present invention may be embodied in other specific forms without departing from the spirit or essential attributes thereof and, accordingly, reference should be made to the appended claims, rather than to the foregoing specification as indicating the scope of the invention.

---

We claim:

1. A purified and isolated cryET1 gene having a nucleotide base sequence coding for the amino acid sequence (SEQ ID NO:2) illustrated in FIG. 1.

2. A purified and isolated cryET1 gene according to claim 1 wherein the gene has a coding region extending from nucleotide bases 177 to 3689 in the nucleotide base sequence illustrated in FIG. 1 (SEQ ID NO:1).

3. A recombinant plasmid containing the gene of claim 1 or 2.

4. A biologically pure culture of a bacterium transformed with the recombinant plasmid of claim 3 which expresses the cryET1 gene.

5. The bacterium of claim 4 wherein the bacterium is *Bacillus thuringiensis*.

6. The *Bacillus thuringiensis* bacterium of claim 5 deposited with the NRRL having accession number NRRL B-18972 and being designated as strain EG7094, or mutants thereof having activity against Plutella xylostella insects.

7. A biologically pure culture of a *Bacillus thuringiensis* bacterium deposited with the NRRL having accession number NRRL B-18973 and being designated as strain EG5092, or mutants thereof having insecticidal activity against Plutella xylostella.

8. An insecticide composition comprising the bacterium of claim 4, an insecticidal protein having insecticidal activity against Plutella xylostella insects and produced by such bacterium, and an agriculturally acceptable carrier.

9. An insecticide composition comprising the bacterium of claim 7, an insecticidal protein produced by such bacterium, and an agriculturally acceptable carrier.

10. A method of controlling susceptible lepidopteran insects comprising applying to a host plant for such insects an insect-controlling effective amount of an insecticidal protein identical to a protein produced by a *Bacillus thuringiensis* bacterium deposited with the NRRL having accession number NRRL B-18972 and being designated as strain EG7094, having activity against Plutella xylostella insects.

11. The method of claim 10 wherein the insecticidal protein is associated with a *Bacillus thuringiensis* bacterium which has produced such protein.

12. The method of claim 10 wherein the lepidopteran insect is *Plutella xylostella*.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 3766 base pairs
( B ) TYPE: nucleic acid
( C ) STRANDEDNESS: double
( D ) TOPOLOGY: circular ( i i ) MOLECULE TYPE: DNA (genomic)

( i x ) FEATURE:
( A ) NAME/KEY: CDS
( B ) LOCATION: 177..3689

( x i ) SEQUENCE DESCRIPTION: SEQ ID NO:1:

```
AATGATACAA  CCTAAATTTT  CATATGTTAA  ACAAGGTTAT  ATGCTGAAAT  ATAAAAAAAT      60

AAGTTGCATA  TTGTGCATAA  ATTCATAATA  TAAATCATAC  GTTTAAAGT   GTTGTGAAGA     120

AAGGAGTATC  GAACTTTTAA  AATTTTTTAT  TTTAACCAAA  GAGAAAGGGG  TAACTT         176

ATG  GAG  ATA  AAT  AAT  CAG  AAC  CAA  TGC  ATA  CCA  TAT  AAT  TGC  TTA  AGT      224
Met  Glu  Ile  Asn  Asn  Gln  Asn  Gln  Cys  Ile  Pro  Tyr  Asn  Cys  Leu  Ser
  1              5                      10                      15

AAT  CCT  GAG  GAA  GTA  CTT  TTG  GAT  GGG  GAG  AGG  ATA  TTA  CCT  GAT  ATC      272
Asn  Pro  Glu  Glu  Val  Leu  Leu  Asp  Gly  Glu  Arg  Ile  Leu  Pro  Asp  Ile
             20                      25                      30

GAT  CCA  CTC  GAA  GTT  TCT  ATG  TCG  CTT  TTG  CAA  TTT  CTT  TTG  AAT  AAC      320
Asp  Pro  Leu  Glu  Val  Ser  Met  Ser  Leu  Leu  Gln  Phe  Leu  Leu  Asn  Asn
                 35                      40                      45

TTT  GTT  CCA  GGG  GGG  GGC  TTT  ATT  TCA  GGA  TTA  TTT  GAT  AAA  ATA  TGG      368
Phe  Val  Pro  Gly  Gly  Gly  Phe  Ile  Ser  Gly  Leu  Phe  Asp  Lys  Ile  Trp
         50                      55                      60

GGG  GCT  TTG  AGA  CCA  TCT  GAC  TGG  GAA  TTA  TTT  CTT  GCA  CAA  ATT  GAA      416
Gly  Ala  Leu  Arg  Pro  Ser  Asp  Trp  Glu  Leu  Phe  Leu  Ala  Gln  Ile  Glu
 65                      70                      75                      80

CAG  TTG  ATT  GAT  CAA  AGA  ATA  GAA  GCA  ACA  GTA  AGA  GCA  AAA  GCA  ATC      464
Gln  Leu  Ile  Asp  Gln  Arg  Ile  Glu  Ala  Thr  Val  Arg  Ala  Lys  Ala  Ile
                 85                      90                      95

GCT  GAA  TTA  GAA  GGT  TTA  GGG  AGA  AGT  TTT  CAA  CTA  TAT  GTA  GAG  GCA      512
Ala  Glu  Leu  Glu  Gly  Leu  Gly  Arg  Ser  Phe  Gln  Leu  Tyr  Val  Glu  Ala
            100                     105                     110

TTT  AAA  GAA  TGG  GAA  GAA  ACT  CCA  GAT  AAC  ACA  GCG  GCT  CGG  TCT  AGA      560
Phe  Lys  Glu  Trp  Glu  Glu  Thr  Pro  Asp  Asn  Thr  Ala  Ala  Arg  Ser  Arg
        115                     120                     125

GTA  ACT  GAG  AGA  TTT  CGT  ATA  ATT  GAT  GCT  CAA  ATT  GAA  GCA  AAT  ATC      608
Val  Thr  Glu  Arg  Phe  Arg  Ile  Ile  Asp  Ala  Gln  Ile  Glu  Ala  Asn  Ile
        130                     135                     140

CCT  TCG  TTT  CGG  ATT  CCC  GGA  TTT  GAA  GTG  CCA  CTT  CTA  TCG  GTT  TAT      656
Pro  Ser  Phe  Arg  Ile  Pro  Gly  Phe  Glu  Val  Pro  Leu  Leu  Ser  Val  Tyr
145                     150                     155                     160
```

-continued

| | | | | | | | | | | | | | | | | |
|---|---|---|---|---|---|---|---|---|---|---|---|---|---|---|---|---|
| GCT | CAA | GCA | GCT | AAT | TTG | CAT | CTC | GCT | CTA | TTA | AGA | GAT | TCT | GTT | ATT | 704 |
| Ala | Gln | Ala | Ala | Asn 165 | Leu | His | Leu | Ala | Leu 170 | Leu | Arg | Asp | Ser | Val 175 | Ile | |
| TTC | GGA | GAG | AGA | TGG | GGA | TTG | ACG | ACT | ACA | AAT | GTC | AAT | GAT | ATC | TAT | 752 |
| Phe | Gly | Glu | Arg 180 | Trp | Gly | Leu | Thr | Thr 185 | Thr | Asn | Val | Asn | Asp 190 | Ile | Tyr | |
| AAT | AGA | CAA | GTT | AAG | AGA | ATT | CAT | GAA | TAT | AGC | GAT | CAT | TGT | GTA | GAT | 800 |
| Asn | Arg | Gln 195 | Val | Lys | Arg | Ile | His 200 | Glu | Tyr | Ser | Asp | His 205 | Cys | Val | Asp | |
| ACG | TAT | AAA | ACA | GAA | TTA | GAA | CGT | CTA | GGG | TTT | ACT | TCT | AGA | GCG | CAG | 848 |
| Thr | Tyr 210 | Lys | Thr | Glu | Leu | Glu 215 | Arg | Leu | Gly | Phe | Thr 220 | Ser | Arg | Ala | Gln | |
| TGG | AAA | ATA | TAT | AAT | CAG | TTT | AGA | AGA | GAA | TTA | ACA | CTA | ACG | GTA | TTA | 896 |
| Trp 225 | Lys | Ile | Tyr | Asn | Gln 230 | Phe | Arg | Arg | Glu | Leu 235 | Thr | Leu | Thr | Val | Leu 240 | |
| GAT | ATT | GTC | GCT | GTT | TTC | CCG | AAC | TAT | GAT | GGT | AAA | CTG | TAT | CCG | ATC | 944 |
| Asp | Ile | Val | Ala | Val 245 | Phe | Pro | Asn | Tyr | Asp 250 | Gly | Lys | Leu | Tyr | Pro 255 | Ile | |
| CAA | ACA | AAA | TCT | GAA | TTA | ACA | AGA | GAA | ATT | TAT | ACA | TCC | CCA | GTA | TCC | 992 |
| Gln | Thr | Lys | Ser 260 | Glu | Leu | Thr | Arg | Glu 265 | Ile | Tyr | Thr | Ser | Pro 270 | Val | Ser | |
| GAA | TAT | TAT | TAT | GGT | GCT | ATT | AAT | AAC | TAT | AAT | CAA | AAT | GGT | ATC | CAA | 1040 |
| Glu | Tyr | Tyr 275 | Tyr | Gly | Ala | Ile | Asn 280 | Asn | Tyr | Asn | Gln | Asn 285 | Gly | Ile | Gln | |
| ACT | GAA | CGG | CAG | ATA | AGG | CAA | CCA | CAT | CTT | ATG | GAC | TTC | TTT | AAC | ACC | 1088 |
| Thr | Glu 290 | Arg | Gln | Ile | Arg | Gln 295 | Pro | His | Leu | Met | Asp 300 | Phe | Phe | Asn | Thr | |
| ATG | ACC | ATG | TAT | ACA | TCA | TAT | AAT | AGA | CGG | GAA | TAT | TAT | TGG | TCA | GGA | 1136 |
| Met 305 | Thr | Met | Tyr | Thr | Ser 310 | Tyr | Asn | Arg | Arg | Glu 315 | Tyr | Tyr | Trp | Ser | Gly 320 | |
| CTT | GAA | ATG | ACG | GCT | TAT | TTC | ACA | GGA | TTT | GCA | GGA | CCT | CAA | GTG | TCA | 1184 |
| Leu | Glu | Met | Thr | Ala 325 | Tyr | Phe | Thr | Gly | Phe 330 | Ala | Gly | Pro | Gln | Val 335 | Ser | |
| TTC | CCT | TTA | GCT | GGG | ACT | AGA | GGG | GAT | GCA | GCT | CCA | CCA | TTT | AAT | GTT | 1232 |
| Phe | Pro | Leu | Ala 340 | Gly | Thr | Arg | Gly | Asp 345 | Ala | Ala | Pro | Pro | Phe 350 | Asn | Val | |
| AGA | AGT | GTT | AAT | GAT | GGA | ATT | TAT | AGA | ATA | TTA | TCG | GCA | CCA | TTT | TAT | 1280 |
| Arg | Ser | Val 355 | Asn | Asp | Gly | Ile | Tyr 360 | Arg | Ile | Leu | Ser | Ala 365 | Pro | Phe | Tyr | |
| TCA | GCA | CCT | TTC | TTA | GGT | ACC | TCT | GTA | TTG | GGC | AGT | CGT | GGA | GAA | GAA | 1328 |
| Ser | Ala 370 | Pro | Phe | Leu | Gly | Thr 375 | Ser | Val | Leu | Gly | Ser 380 | Arg | Gly | Glu | Glu | |
| TTT | ATG | TTT | GCA | CTT | AAT | AAT | ATT | TCA | CCC | CCG | CCA | TCT | GCA | AGA | TAC | 1376 |
| Phe | Met 385 | Phe | Ala | Leu | Asn | Asn 390 | Ile | Ser | Pro | Pro | Pro 395 | Ser | Ala | Arg | Tyr 400 | |
| AGA | AAT | CCT | GGA | ACA | GTA | GAT | TCA | CTA | GTC | AGC | ATA | CCG | CCA | CAG | GAT | 1424 |
| Arg | Asn | Pro | Gly | Thr 405 | Val | Asp | Ser | Leu | Val 410 | Ser | Ile | Pro | Pro | Gln 415 | Asp | |
| AAT | AGC | GTG | CCA | CCA | CAC | AGG | GGA | TCT | AGT | CAT | CGA | TTA | AGT | CAT | GTT | 1472 |
| Asn | Ser | Val | Pro 420 | Pro | His | Arg | Gly | Ser 425 | Ser | His | Arg | Leu | Ser 430 | His | Val | |
| ACA | ATG | CGT | AAT | AGT | TCA | CCT | ATA | TTC | CAC | TGG | ACA | CAT | CGC | AGC | GCA | 1520 |
| Thr | Met | Arg 435 | Asn | Ser | Ser | Pro | Ile 440 | Phe | His | Trp | Thr | His 445 | Arg | Ser | Ala | |
| ACC | ACT | ACA | AAT | AGA | ATT | AAT | TCA | GAT | GTT | ATT | ACG | CAA | ATT | CCA | ATG | 1568 |
| Thr | Thr | Thr 450 | Asn | Arg | Ile | Asn | Ser 455 | Asp | Val | Ile | Thr | Gln 460 | Ile | Pro | Met | |
| GTA | AAA | GCA | TAC | AAT | CTT | CAT | GCA | GGT | GCC | ACT | GTT | GTT | AGA | GGA | CCC | 1616 |
| Val | Lys 465 | Ala | Tyr | Asn | Leu | His 470 | Ala | Gly | Ala | Thr | Val 475 | Val | Arg | Gly | Pro 480 | |
| GGG | TTT | ACA | GGT | GGT | GAT | ATC | CTG | AGA | CGA | ACA | AGT | AAT | GGG | ATG | GTC | 1664 |
| Gly | Phe | Thr | Gly | Gly | Asp | Ile | Leu | Arg | Arg | Thr | Ser | Asn | Gly | Met | Val | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 485 |     |     |     |     | 490 |     |     |     |     |     | 495 |     |      |
| GTA | ACA | CTA | AGA | GTA | GAT | GCC | TCT | GCA | GTA | AGG | AAC | CAA | CGA | TAT | CGC | 1712 |
| Val | Thr | Leu | Arg | Val | Asp | Ala | Ser | Ala | Val | Arg | Asn | Gln | Arg | Tyr | Arg |      |
|     |     |     | 500 |     |     |     |     | 505 |     |     |     |     | 510 |     |     |      |
| ATA | AGA | TTC | CGT | TAT | GCT | GCA | ACA | TCA | AAT | TTC | TAT | TTT | GTC | GTA | AGG | 1760 |
| Ile | Arg | Phe | Arg | Tyr | Ala | Ala | Thr | Ser | Asn | Phe | Tyr | Phe | Val | Val | Arg |      |
|     |     | 515 |     |     |     |     |     | 520 |     |     |     |     | 525 |     |     |      |
| CGT | GGG | AAT | CTT | GGT | GTT | AAT | GGT | CGA | GAG | ATC | ATG | AAA | ACA | ATG | AGT | 1808 |
| Arg | Gly | Asn | Leu | Gly | Val | Asn | Gly | Arg | Glu | Ile | Met | Lys | Thr | Met | Ser |      |
|     | 530 |     |     |     |     | 535 |     |     |     |     | 540 |     |     |     |     |      |
| ACA | GGC | GAG | GAA | TTA | AAA | TCT | GCA | TCT | TTT | GTT | TTG | GGA | GAG | TTT | ATT | 1856 |
| Thr | Gly | Glu | Glu | Leu | Lys | Ser | Ala | Ser | Phe | Val | Leu | Gly | Glu | Phe | Ile |      |
| 545 |     |     |     |     | 550 |     |     |     |     | 555 |     |     |     |     | 560 |      |
| ACG | CCT | TTT | AAT | TTT | TTT | GAA | AAT | CAG | GTT | CCA | CTT | CAA | ATA | GAA | ATA | 1904 |
| Thr | Pro | Phe | Asn | Phe | Phe | Glu | Asn | Gln | Val | Pro | Leu | Gln | Ile | Glu | Ile |      |
|     |     |     |     | 565 |     |     |     |     | 570 |     |     |     |     | 575 |     |      |
| CAA | TCA | CTT | TCT | CCT | GGG | GGA | GAG | GTG | TAT | CTG | GAC | AAA | ATT | GAA | TTC | 1952 |
| Gln | Ser | Leu | Ser | Pro | Gly | Gly | Glu | Val | Tyr | Leu | Asp | Lys | Ile | Glu | Phe |      |
|     |     |     | 580 |     |     |     |     | 585 |     |     |     |     | 590 |     |     |      |
| ATC | CCA | GCA | GAT | ACA | ACA | TTT | GAA | GCA | GAA | TAT | GAT | TTA | GAA | AGA | GCG | 2000 |
| Ile | Pro | Ala | Asp | Thr | Thr | Phe | Glu | Ala | Glu | Tyr | Asp | Leu | Glu | Arg | Ala |      |
|     |     || 595 |     |     |     |     | 600 |     |     |     |     | 605 |     |     |      |
| CAG | AAG | GCG | GTG | AAT | GCT | CTG | TTT | ACT | TCT | ACG | AAT | CAA | AGA | GGA | CTA | 2048 |
| Gln | Lys | Ala | Val | Asn | Ala | Leu | Phe | Thr | Ser | Thr | Asn | Gln | Arg | Gly | Leu |      |
|     |     | 610 |     |     |     |     | 615 |     |     |     |     | 620 |     |     |     |      |
| AAA | ACA | GAT | GTA | ACA | GAT | TAT | CAC | ATT | GAT | CAA | GTA | TCC | AAT | TTA | GTC | 2096 |
| Lys | Thr | Asp | Val | Thr | Asp | Tyr | His | Ile | Asp | Gln | Val | Ser | Asn | Leu | Val |      |
| 625 |     |     |     |     | 630 |     |     |     |     | 635 |     |     |     |     | 640 |      |
| GAA | TGT | TTA | TCG | GAT | GAA | TTT | TGT | TTA | GAT | GAA | AAG | AGA | GAG | TTG | TCC | 2144 |
| Glu | Cys | Leu | Ser | Asp | Glu | Phe | Cys | Leu | Asp | Glu | Lys | Arg | Glu | Leu | Ser |      |
|     |     |     |     | 645 |     |     |     |     | 650 |     |     |     |     | 655 |     |      |
| GAG | AAA | GTC | AAA | CAT | GCG | AAG | CGA | CTC | AGT | GAT | GAA | AGA | AAC | TTA | CTG | 2192 |
| Glu | Lys | Val | Lys | His | Ala | Lys | Arg | Leu | Ser | Asp | Glu | Arg | Asn | Leu | Leu |      |
|     |     |     | 660 |     |     |     |     | 665 |     |     |     |     | 670 |     |     |      |
| CAA | GAT | CCA | AAC | TTC | ACA | TCC | ATC | AAT | GGA | CAA | CTA | GAC | CGT | GGA | TGG | 2240 |
| Gln | Asp | Pro | Asn | Phe | Thr | Ser | Ile | Asn | Gly | Gln | Leu | Asp | Arg | Gly | Trp |      |
|     |     | 675 |     |     |     |     | 680 |     |     |     |     | 685 |     |     |     |      |
| AGA | GGA | AGT | ACG | GAT | ATT | ACC | ATC | CAA | GGA | GGA | AAT | GAC | GTA | TTC | AAA | 2288 |
| Arg | Gly | Ser | Thr | Asp | Ile | Thr | Ile | Gln | Gly | Gly | Asn | Asp | Val | Phe | Lys |      |
|     | 690 |     |     |     |     | 695 |     |     |     |     | 700 |     |     |     |     |      |
| GAA | AAT | TAC | GTC | ACA | CTA | CCA | GGT | ACC | TTT | GAT | GAG | TGT | TAT | CCA | ACG | 2336 |
| Glu | Asn | Tyr | Val | Thr | Leu | Pro | Gly | Thr | Phe | Asp | Glu | Cys | Tyr | Pro | Thr |      |
| 705 |     |     |     |     | 710 |     |     |     |     | 715 |     |     |     |     | 720 |      |
| TAT | TTG | TAT | CAA | AAA | ATA | GAT | GAG | TCA | AAA | TTA | AAA | GCC | TAT | ACT | CGC | 2384 |
| Tyr | Leu | Tyr | Gln | Lys | Ile | Asp | Glu | Ser | Lys | Leu | Lys | Ala | Tyr | Thr | Arg |      |
|     |     |     |     | 725 |     |     |     |     | 730 |     |     |     |     | 735 |     |      |
| TAT | GAA | TTA | AGA | GGA | TAT | ATT | GAA | GAT | AGT | CAA | GAT | CTA | GAG | GTT | TAT | 2432 |
| Tyr | Glu | Leu | Arg | Gly | Tyr | Ile | Glu | Asp | Ser | Gln | Asp | Leu | Glu | Val | Tyr |      |
|     |     |     | 740 |     |     |     |     | 745 |     |     |     |     | 750 |     |     |      |
| TTA | ATT | CGT | TAC | AAT | GCA | AAA | CAT | GAA | ACG | CTA | AAT | GTT | CCA | GGT | ACC | 2480 |
| Leu | Ile | Arg | Tyr | Asn | Ala | Lys | His | Glu | Thr | Leu | Asn | Val | Pro | Gly | Thr |      |
|     |     | 755 |     |     |     |     | 760 |     |     |     |     | 765 |     |     |     |      |
| GAC | TCC | TTA | CGG | ACG | CTT | TCA | GTT | GAA | AGC | CAA | AAC | GGA | AGG | TGT | GGA | 2528 |
| Asp | Ser | Leu | Arg | Thr | Leu | Ser | Val | Glu | Ser | Gln | Asn | Gly | Arg | Cys | Gly |      |
|     | 770 |     |     |     |     | 775 |     |     |     |     | 780 |     |     |     |     |      |
| GAA | CTG | AAT | CGA | TGT | ATG | CCA | CAT | ATT | AAA | TGG | AAT | CCT | GAT | GTA | GAT | 2576 |
| Glu | Leu | Asn | Arg | Cys | Met | Pro | His | Ile | Lys | Trp | Asn | Pro | Asp | Val | Asp |      |
| 785 |     |     |     |     | 790 |     |     |     |     | 795 |     |     |     |     | 800 |      |
| TGT | TCC | TGC | AGA | GAC | GGA | GAG | AAG | TGT | GCC | CAT | CAT | TCC | CAT | CAT | TTC | 2624 |
| Cys | Ser | Cys | Arg | Asp | Gly | Glu | Lys | Cys | Ala | His | His | Ser | His | His | Phe |      |
|     |     |     |     | 805 |     |     |     |     | 810 |     |     |     |     | 815 |     |      |

```
TCC CTA GAC ATT GAT GTT GGA TGC ACA GAC TTG CAA GAG GAT TTA GGC    2672
Ser Leu Asp Ile Asp Val Gly Cys Thr Asp Leu Gln Glu Asp Leu Gly
        820             825             830

GTG TGG GTT GTA TTC AAG ATT AAG ACG CAG GAA GGT TAT GCA AGA TTA    2720
Val Trp Val Val Phe Lys Ile Lys Thr Gln Glu Gly Tyr Ala Arg Leu
        835             840             845

GGA AAT CTG GAA TTC ATC GAA GAG AAA CCA TTA GTA GGA GAA GCA CTG    2768
Gly Asn Leu Glu Phe Ile Glu Glu Lys Pro Leu Val Gly Glu Ala Leu
        850             855             860

TCT CGT GTG AAG AGA GCG GAG AAA AAA TGG AGA GAC AAA CGT GAA AAA    2816
Ser Arg Val Lys Arg Ala Glu Lys Lys Trp Arg Asp Lys Arg Glu Lys
865             870             875             880

TTG GAA TTG GAA ACA AAA CGA GTA TAT ACA GAG GCA AAA GAA GCT GTG    2864
Leu Glu Leu Glu Thr Lys Arg Val Tyr Thr Glu Ala Lys Glu Ala Val
                885             890             895

GAT GCT TTA TTC GTA GAT TCT CAA TAT GAT AGA TTA CAA GCA GAT ACA    2912
Asp Ala Leu Phe Val Asp Ser Gln Tyr Asp Arg Leu Gln Ala Asp Thr
            900             905             910

AAC ATT GGT ATG ATT CAT GCG GCA GAT AAA CTT GTT CAT CGA ATC TGC    2960
Asn Ile Gly Met Ile His Ala Ala Asp Lys Leu Val His Arg Ile Cys
            915             920             925

GAG ACT TAT CTT CCA GAA CTA CCT TTC ATT CCA GGA ATA AAC GCG ATA    3008
Glu Thr Tyr Leu Pro Glu Leu Pro Phe Ile Pro Gly Ile Asn Ala Ile
        930             935             940

ATT TTT GAA GAA TTA GAA AAT CGT ATT TCC ACT GCA TTC TTC CTA TAC    3056
Ile Phe Glu Glu Leu Glu Asn Arg Ile Ser Thr Ala Phe Phe Leu Tyr
945             950             955             960

GAA GCA AGA AAT GTT ATT AAC AAT GGG GAT TTT AAT AAT GGA TTA ACA    3104
Glu Ala Arg Asn Val Ile Asn Asn Gly Asp Phe Asn Asn Gly Leu Thr
                965             970             975

TGC TGG AAC GTG AAA GGT CAT GTA GAT GTA CAA CAG AGC CAT CAT CGT    3152
Cys Trp Asn Val Lys Gly His Val Asp Val Gln Gln Ser His His Arg
            980             985             990

TCT GTC CTT GTT ATC CCA GAA TGG GAA GCA GAA GTG TCA CAA AAA GTT    3200
Ser Val Leu Val Ile Pro Glu Trp Glu Ala Glu Val Ser Gln Lys Val
            995             1000            1005

CGT GTA TGT CCA GGT CGT GGA TAC ATC CTT CGT GTC ACA GCG TAC AAA    3248
Arg Val Cys Pro Gly Arg Gly Tyr Ile Leu Arg Val Thr Ala Tyr Lys
        1010            1015            1020

GAG GGC TAC GGA GAA GGA TGC GTA ACG ATC CAT GAG ATC GAA GAC AAC    3296
Glu Gly Tyr Gly Glu Gly Cys Val Thr Ile His Glu Ile Glu Asp Asn
1025            1030            1035            1040

ACA GAC GAA CTG AAG TTT AGA AAC TGT GAA GAA GAG GGA GAT TAT TCA    3344
Thr Asp Glu Leu Lys Phe Arg Asn Cys Glu Glu Glu Gly Asp Tyr Ser
                1045            1050            1055

AAC GAC ACA GGA ACG TGT AAT GAT TAT CCT GCA TCC CAA GGT GCA GCA    3392
Asn Asp Thr Gly Thr Cys Asn Asp Tyr Pro Ala Ser Gln Gly Ala Ala
            1060            1065            1070

GGC TGC GCA GAT GTA TGT AAT TCC CGT AAT GTT GGA TAT AAG GAT GCA    3440
Gly Cys Ala Asp Val Cys Asn Ser Arg Asn Val Gly Tyr Lys Asp Ala
            1075            1080            1085

TAT GAA ACG AAT ACC TCA GCA TCT GTT AAT TAC AAA CCG ACT TAC GAA    3488
Tyr Glu Thr Asn Thr Ser Ala Ser Val Asn Tyr Lys Pro Thr Tyr Glu
        1090            1095            1100

GAA GAA ACG TAT ACA GAT GTA CGA GAA GAT AAT CAT TGT GAA TAT GAC    3536
Glu Glu Thr Tyr Thr Asp Val Arg Glu Asp Asn His Cys Glu Tyr Asp
1105            1110            1115            1120

AGA GGG TAT GTG AAT TAT CCA CCA TTA CCA GCT GGT TAT GTG ACA AAA    3584
Arg Gly Tyr Val Asn Tyr Pro Pro Leu Pro Ala Gly Tyr Val Thr Lys
                1125            1130            1135

GAA TTA GAA TAC TTC CCT GAA ACA GAT ACA GTA TGG ATT GAG ATT GGA    3632
Glu Leu Glu Tyr Phe Pro Glu Thr Asp Thr Val Trp Ile Glu Ile Gly
```

|  | 1140 |  |  |  | 1145 |  |  |  | 1150 |  |  |  |
|---|---|---|---|---|---|---|---|---|---|---|---|---|

GAA ACG GAA GGG AAG TTT ATT GTA GAC AGT GTC GAA TTA CTC CTT ATG                3680
Glu Thr Glu Gly Lys Phe Ile Val Asp Ser Val Glu Leu Leu Leu Met
        1155              1160              1165

GAA GAA TAGAATCCAA AAATAGTCGC TTAACCTCCG TTACAAATAA ATACGTAAAC                3736
Glu Glu
1170

CGTTGTAGCA AAAAGAAAAA TGGACTTGTC                                              3766

(2) INFORMATION FOR SEQ ID NO:2:

(i) SEQUENCE CHARACTERISTICS:
        (A) LENGTH: 1170 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Ile Asn Asn Gln Asn Gln Cys Ile Pro Tyr Asn Cys Leu Ser
 1               5                  10                  15

Asn Pro Glu Glu Val Leu Leu Asp Gly Glu Arg Ile Leu Pro Asp Ile
            20                  25                  30

Asp Pro Leu Glu Val Ser Met Ser Leu Leu Gln Phe Leu Leu Asn Asn
        35                  40                  45

Phe Val Pro Gly Gly Gly Phe Ile Ser Gly Leu Phe Asp Lys Ile Trp
    50                  55                  60

Gly Ala Leu Arg Pro Ser Asp Trp Glu Leu Phe Leu Ala Gln Ile Glu
65                  70                  75                  80

Gln Leu Ile Asp Gln Arg Ile Glu Ala Thr Val Arg Ala Lys Ala Ile
                85                  90                  95

Ala Glu Leu Glu Gly Leu Gly Arg Ser Phe Gln Leu Tyr Val Glu Ala
            100                 105                 110

Phe Lys Glu Trp Glu Glu Thr Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Ile Pro Gly Phe Glu Val Pro Leu Leu Ser Val Tyr
145                 150                 155                 160

Ala Gln Ala Ala Asn Leu His Leu Ala Leu Leu Arg Asp Ser Val Ile
                165                 170                 175

Phe Gly Glu Arg Trp Gly Leu Thr Thr Thr Asn Val Asn Asp Ile Tyr
            180                 185                 190

Asn Arg Gln Val Lys Arg Ile His Glu Tyr Ser Asp His Cys Val Asp
        195                 200                 205

Thr Tyr Lys Thr Glu Leu Glu Arg Leu Gly Phe Thr Ser Arg Ala Gln
    210                 215                 220

Trp Lys Ile Tyr Asn Gln Phe Arg Arg Glu Leu Thr Leu Thr Val Leu
225                 230                 235                 240

Asp Ile Val Ala Val Phe Pro Asn Tyr Asp Gly Lys Leu Tyr Pro Ile
                245                 250                 255

Gln Thr Lys Ser Glu Leu Thr Arg Glu Ile Tyr Thr Ser Pro Val Ser
            260                 265                 270

Glu Tyr Tyr Tyr Gly Ala Ile Asn Asn Tyr Asn Gln Asn Gly Ile Gln
        275                 280                 285

Thr Glu Arg Gln Ile Arg Gln Pro His Leu Met Asp Phe Phe Asn Thr
    290                 295                 300

Met Thr Met Tyr Thr Ser Tyr Asn Arg Arg Glu Tyr Tyr Trp Ser Gly

-continued

| | | | 305 | | | | 310 | | | | 315 | | | | 320 |
|---|---|---|---|---|---|---|---|---|---|---|---|---|---|---|---|
| Leu | Glu | Met | Thr | Ala | Tyr | Phe | Thr | Gly | Phe | Ala | Gly | Pro | Gln | Val | Ser |
| | | | 325 | | | | 330 | | | | 335 | | | | |
| Phe | Pro | Leu | Ala | Gly | Thr | Arg | Gly | Asp | Ala | Ala | Pro | Pro | Phe | Asn | Val |
| | | | 340 | | | | 345 | | | | 350 | | | | |
| Arg | Ser | Val | Asn | Asp | Gly | Ile | Tyr | Arg | Ile | Leu | Ser | Ala | Pro | Phe | Tyr |
| | | | 355 | | | | 360 | | | | 365 | | | | |
| Ser | Ala | Pro | Phe | Leu | Gly | Thr | Ser | Val | Leu | Gly | Ser | Arg | Gly | Glu | Glu |
| | | | 370 | | | | 375 | | | | 380 | | | | |
| Phe | Met | Phe | Ala | Leu | Asn | Asn | Ile | Ser | Pro | Pro | Ser | Ala | Arg | Tyr |
| 385 | | | | | 390 | | | | 395 | | | | | 400 |
| Arg | Asn | Pro | Gly | Thr | Val | Asp | Ser | Leu | Val | Ser | Ile | Pro | Pro | Gln | Asp |
| | | | 405 | | | | 410 | | | | 415 | | | | |
| Asn | Ser | Val | Pro | Pro | His | Arg | Gly | Ser | Ser | His | Arg | Leu | Ser | His | Val |
| | | | 420 | | | | 425 | | | | 430 | | | | |
| Thr | Met | Arg | Asn | Ser | Ser | Pro | Ile | Phe | His | Trp | Thr | His | Arg | Ser | Ala |
| | | | 435 | | | | 440 | | | | 445 | | | | |
| Thr | Thr | Thr | Asn | Arg | Ile | Asn | Ser | Asp | Val | Ile | Thr | Gln | Ile | Pro | Met |
| | | | 450 | | | | 455 | | | | 460 | | | | |
| Val | Lys | Ala | Tyr | Asn | Leu | His | Ala | Gly | Ala | Thr | Val | Val | Arg | Gly | Pro |
| 465 | | | | | 470 | | | | 475 | | | | | 480 |
| Gly | Phe | Thr | Gly | Gly | Asp | Ile | Leu | Arg | Arg | Thr | Ser | Asn | Gly | Met | Val |
| | | | 485 | | | | 490 | | | | 495 | | | | |
| Val | Thr | Leu | Arg | Val | Asp | Ala | Ser | Ala | Val | Arg | Asn | Gln | Arg | Tyr | Arg |
| | | | 500 | | | | 505 | | | | 510 | | | | |
| Ile | Arg | Phe | Arg | Tyr | Ala | Ala | Thr | Ser | Asn | Phe | Tyr | Phe | Val | Val | Arg |
| | | | 515 | | | | 520 | | | | 525 | | | | |
| Arg | Gly | Asn | Leu | Gly | Val | Asn | Gly | Arg | Glu | Ile | Met | Lys | Thr | Met | Ser |
| | 530 | | | | | 535 | | | | 540 | | | | | |
| Thr | Gly | Glu | Glu | Leu | Lys | Ser | Ala | Ser | Phe | Val | Leu | Gly | Glu | Phe | Ile |
| 545 | | | | | 550 | | | | 555 | | | | | | 560 |
| Thr | Pro | Phe | Asn | Phe | Glu | Asn | Gln | Val | Pro | Leu | Gln | Ile | Glu | Ile |
| | | | | 565 | | | | 570 | | | | | | 575 |
| Gln | Ser | Leu | Ser | Pro | Gly | Gly | Glu | Val | Tyr | Leu | Asp | Lys | Ile | Glu | Phe |
| | | | 580 | | | | 585 | | | | 590 | | | | |
| Ile | Pro | Ala | Asp | Thr | Thr | Phe | Glu | Ala | Glu | Tyr | Asp | Leu | Glu | Arg | Ala |
| | | | 595 | | | | 600 | | | | 605 | | | | |
| Gln | Lys | Ala | Val | Asn | Ala | Leu | Phe | Thr | Ser | Thr | Asn | Gln | Arg | Gly | Leu |
| | 610 | | | | | 615 | | | | 620 | | | | | |
| Lys | Thr | Asp | Val | Thr | Asp | Tyr | His | Ile | Asp | Gln | Val | Ser | Asn | Leu | Val |
| 625 | | | | | 630 | | | | 635 | | | | | | 640 |
| Glu | Cys | Leu | Ser | Asp | Glu | Phe | Cys | Leu | Asp | Glu | Lys | Arg | Glu | Leu | Ser |
| | | | | 645 | | | | 650 | | | | | | 655 |
| Glu | Lys | Val | Lys | His | Ala | Lys | Arg | Leu | Ser | Asp | Glu | Arg | Asn | Leu | Leu |
| | | | 660 | | | | 665 | | | | 670 | | | | |
| Gln | Asp | Pro | Asn | Phe | Thr | Ser | Ile | Asn | Gly | Gln | Leu | Asp | Arg | Gly | Trp |
| | | | 675 | | | | 680 | | | | 685 | | | | |
| Arg | Gly | Ser | Thr | Asp | Ile | Thr | Ile | Gln | Gly | Gly | Asn | Asp | Val | Phe | Lys |
| | 690 | | | | | 695 | | | | 700 | | | | | |
| Glu | Asn | Tyr | Val | Thr | Leu | Pro | Gly | Thr | Phe | Asp | Glu | Cys | Tyr | Pro | Thr |
| 705 | | | | | 710 | | | | 715 | | | | | | 720 |
| Tyr | Leu | Tyr | Gln | Lys | Ile | Asp | Glu | Ser | Lys | Leu | Lys | Ala | Tyr | Thr | Arg |
| | | | | 725 | | | | 730 | | | | | | 735 |
| Tyr | Glu | Leu | Arg | Gly | Tyr | Ile | Glu | Asp | Ser | Gln | Asp | Leu | Glu | Val | Tyr |
| | | | 740 | | | | 745 | | | | 750 | | | | |

```
Leu  Ile  Arg  Tyr  Asn  Ala  Lys  His  Glu  Thr  Leu  Asn  Val  Pro  Gly  Thr
          755                 760                 765

Asp  Ser  Leu  Arg  Thr  Leu  Ser  Val  Glu  Ser  Gln  Asn  Gly  Arg  Cys  Gly
770                      775                      780

Glu  Leu  Asn  Arg  Cys  Met  Pro  His  Ile  Lys  Trp  Asn  Pro  Asp  Val  Asp
785                      790                      795                      800

Cys  Ser  Cys  Arg  Asp  Gly  Glu  Lys  Cys  Ala  His  His  Ser  His  His  Phe
                    805                 810                      815

Ser  Leu  Asp  Ile  Asp  Val  Gly  Cys  Thr  Asp  Leu  Gln  Glu  Asp  Leu  Gly
               820                      825                      830

Val  Trp  Val  Val  Phe  Lys  Ile  Lys  Thr  Gln  Glu  Gly  Tyr  Ala  Arg  Leu
               835                      840                      845

Gly  Asn  Leu  Glu  Phe  Ile  Glu  Glu  Lys  Pro  Leu  Val  Gly  Glu  Ala  Leu
          850                      855                      860

Ser  Arg  Val  Lys  Arg  Ala  Glu  Lys  Lys  Trp  Arg  Asp  Lys  Arg  Glu  Lys
865                      870                      875                      880

Leu  Glu  Leu  Glu  Thr  Lys  Arg  Val  Tyr  Thr  Glu  Ala  Lys  Glu  Ala  Val
                    885                      890                      895

Asp  Ala  Leu  Phe  Val  Asp  Ser  Gln  Tyr  Asp  Arg  Leu  Gln  Ala  Asp  Thr
               900                      905                      910

Asn  Ile  Gly  Met  Ile  His  Ala  Ala  Asp  Lys  Leu  Val  His  Arg  Ile  Cys
          915                      920                      925

Glu  Thr  Tyr  Leu  Pro  Glu  Leu  Pro  Phe  Ile  Pro  Gly  Ile  Asn  Ala  Ile
930                      935                      940

Ile  Phe  Glu  Glu  Leu  Glu  Asn  Arg  Ile  Ser  Thr  Ala  Phe  Phe  Leu  Tyr
945                      950                      955                      960

Glu  Ala  Arg  Asn  Val  Ile  Asn  Asn  Gly  Asp  Phe  Asn  Asn  Gly  Leu  Thr
                    965                      970                      975

Cys  Trp  Asn  Val  Lys  Gly  His  Val  Asp  Val  Gln  Gln  Ser  His  His  Arg
               980                      985                      990

Ser  Val  Leu  Val  Ile  Pro  Glu  Trp  Glu  Ala  Glu  Val  Ser  Gln  Lys  Val
          995                      1000                     1005

Arg  Val  Cys  Pro  Gly  Arg  Gly  Tyr  Ile  Leu  Arg  Val  Thr  Ala  Tyr  Lys
     1010                     1015                     1020

Glu  Gly  Tyr  Gly  Glu  Gly  Cys  Val  Thr  Ile  His  Glu  Ile  Glu  Asp  Asn
1025                     1030                     1035                     1040

Thr  Asp  Glu  Leu  Lys  Phe  Arg  Asn  Cys  Glu  Glu  Glu  Gly  Asp  Tyr  Ser
               1045                     1050                     1055

Asn  Asp  Thr  Gly  Thr  Cys  Asn  Asp  Tyr  Pro  Ala  Ser  Gln  Gly  Ala  Ala
               1060                     1065                     1070

Gly  Cys  Ala  Asp  Val  Cys  Asn  Ser  Arg  Asn  Val  Gly  Tyr  Lys  Asp  Ala
          1075                     1080                     1085

Tyr  Glu  Thr  Asn  Thr  Ser  Ala  Ser  Val  Asn  Tyr  Lys  Pro  Thr  Tyr  Glu
     1090                     1095                     1100

Glu  Glu  Thr  Tyr  Thr  Asp  Val  Arg  Glu  Asp  Asn  His  Cys  Glu  Tyr  Asp
1105                     1110                     1115                     1120

Arg  Gly  Tyr  Val  Asn  Tyr  Pro  Pro  Leu  Pro  Ala  Gly  Tyr  Val  Thr  Lys
                    1125                     1130                     1135

Glu  Leu  Glu  Tyr  Phe  Pro  Glu  Thr  Asp  Thr  Val  Trp  Ile  Glu  Ile  Gly
               1140                     1145                     1150

Glu  Thr  Glu  Gly  Lys  Phe  Ile  Val  Asp  Ser  Val  Glu  Leu  Leu  Leu  Met
          1155                     1160                     1165

Glu  Glu
     1170
```